(12) United States Patent
Kori et al.

(10) Patent No.: US 8,835,697 B2
(45) Date of Patent: Sep. 16, 2014

(54) BIPHENYL DERIVATIVE, RESIST BOTTOM LAYER MATERIAL, BOTTOM LAYER FORMING METHOD, AND PATTERNING PROCESS

(75) Inventors: Daisuke Kori, Joetsu (JP); Takeshi Kinsho, Joetsu (JP); Katsuya Takemura, Joetsu (JP); Tsutomu Ogihara, Joetsu (JP); Takeru Watanabe, Joetsu (JP); Hiroyuki Urano, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 227 days.

(21) Appl. No.: 13/424,455

(22) Filed: Mar. 20, 2012

(65) Prior Publication Data
US 2012/0252218 A1 Oct. 4, 2012

(30) Foreign Application Priority Data
Mar. 28, 2011 (JP) ................. 2011-069703

(51) Int. Cl.
C07C 39/17 (2006.01)
G03F 7/09 (2006.01)
C09D 161/12 (2006.01)

(52) U.S. Cl.
CPC ............. *C07C 39/17* (2013.01); *G03F 7/091* (2013.01); *C09D 161/12* (2013.01); *G03F 7/094* (2013.01)
USPC ............ 568/719; 568/734; 568/735; 528/219

(58) Field of Classification Search
CPC ... C07D 471/04; A61K 47/10; H01L 51/0052
USPC ................. 568/719, 734, 735; 528/219
See application file for complete search history.

(56) References Cited

U.S. PATENT DOCUMENTS

| | | | |
|---|---|---|---|
| 5,972,560 A | 10/1999 | Kaneko et al. | |
| 6,042,989 A | 3/2000 | Schaedeli et al. | |
| 6,420,088 B1 | 7/2002 | Angelopoulos et al. | |
| 6,506,497 B1 | 1/2003 | Kennedy et al. | |
| 6,576,562 B2 | 6/2003 | Ohuchi et al. | |
| 6,623,909 B2 | 9/2003 | Hatakeyama et al. | |
| 6,749,765 B2 | 6/2004 | Rutter, Jr. et al. | |
| 6,852,791 B2 | 2/2005 | Kawaguchi et al. | |
| 7,094,708 B2 | 8/2006 | Kato et al. | |
| 7,156,923 B2 | 1/2007 | Kato et al. | |
| 7,163,778 B2 | 1/2007 | Hatakeyama et al. | |
| 7,303,855 B2 | 12/2007 | Hatakeyama et al. | |
| 7,358,025 B2 | 4/2008 | Hatakeyama | |
| 7,537,880 B2 | 5/2009 | Harada et al. | |
| 7,745,104 B2 | 6/2010 | Hatakeyama et al. | |
| 8,026,038 B2 | 9/2011 | Ogihara et al. | |
| 2006/0186797 A1* | 8/2006 | Nishiyama et al. ........... | 313/504 |
| 2007/0238300 A1 | 10/2007 | Ogihara et al. | |
| 2010/0099044 A1 | 4/2010 | Hatakeyama et al. | |
| 2013/0302990 A1* | 11/2013 | Watanabe et al. ........... | 438/703 |

FOREIGN PATENT DOCUMENTS

| | | |
|---|---|---|
| JP | 6-118651 A | 4/1994 |
| JP | 9-110938 A | 4/1997 |
| JP | 10-324748 A | 12/1998 |
| JP | 11-154638 A | 6/1999 |
| JP | 2001-40293 A | 2/2001 |
| JP | 2002-14474 A | 1/2002 |
| JP | 2002-47430 A | 2/2002 |
| JP | 2002-55456 A | 2/2002 |
| JP | 2002-214777 A | 7/2002 |
| JP | 2002-334869 A | 11/2002 |
| JP | 3504247 B2 | 3/2004 |
| JP | 2004-205685 A | 7/2004 |
| JP | 2004-310019 A | 11/2004 |
| JP | 2005-128509 A | 5/2005 |

(Continued)

OTHER PUBLICATIONS

Dahl; Organic Letters, 2008, vol. 10, 24, 5605-5608.*

(Continued)

*Primary Examiner* — Sudhakar Katakam
*Assistant Examiner* — Pancham Bakshi
(74) *Attorney, Agent, or Firm* — Westerman, Hattori, Daniels & Adrian, LLP

(57) ABSTRACT

A biphenyl derivative having formula (1) is provided wherein Ar1 and Ar2 denote a benzene or naphthalene ring, and x and z each are 0 or 1. A material comprising the biphenyl derivative or a polymer comprising recurring units of the biphenyl derivative is spin coated and heat treated to form a resist bottom layer having improved properties, optimum values of n and k, step coverage, etch resistance, heat resistance, solvent resistance, and minimized outgassing.

(1)

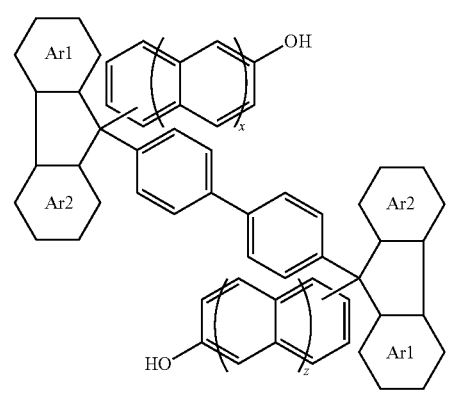

5 Claims, 5 Drawing Sheets

(56) References Cited

FOREIGN PATENT DOCUMENTS

| | | |
|---|---|---|
| JP | 2005-250434 A | 9/2005 |
| JP | 2006-227391 A | 8/2006 |
| JP | 2006-285095 A | 10/2006 |
| JP | 2006-293298 A | 10/2006 |
| JP | 2007-99741 A | 4/2007 |
| JP | 2007-302873 A | 11/2007 |
| JP | 2008-65303 A | 3/2008 |
| JP | 2008-111103 A | 5/2008 |
| JP | 2008-158002 A | 7/2008 |
| JP | 2009-126940 A | 6/2009 |
| JP | 2010-122656 A | 6/2010 |
| WO | 2004/066377 A1 | 8/2004 |

OTHER PUBLICATIONS

Kwong, Ranee et al., "IBM 193nm Bilayer Resist: Materials, Lithographic Performance and Optimization", Proc. of SPIE, 2001, pp. 50-57, vol. 4345, cited in specification.

Moran, J.M. et al., "High resolution, steep profile resist patterns", Vac. Sci. Technol., Nov/Dec 1979, pp. 1620-1624, vol. 16, cited in specification.

Johnson, Donald, "Thermolysis of Positive Photoresist", SPIE, 1984, pp. 72- 79, vol. 469, cited in specification.

Noda, Tokiti et al., "A Comment on the Structure of Glassy Carbon", Glass Carbon Bull. Chem. Soc., 1968, pp. 3023-3024, vol. 41, cited in specification.

Abe, J. et al., "Sub-55-nm Etch Process Using Stacked-Mask Process", Dry Process International Symposium, 2005, pp. 11-12, cited in specification.

Lynch, Tom et al., "Properties and Performance of Near UV Reflectivity Control Layers", Proc. of SPIE, 1994, pp. 225-235, vol. 2195.

* cited by examiner

SUBSTRATE REFLECTANCE
MIDDLE LAYER, n = 1.5, VARIABLE k

□ 0-1  ▨ 1-2  ▨ 2-3  ▨ 3-4  ■ 4-5      SUBSTRATE REFLECTANCE (%)

SUBSTRATE REFLECTANCE
MIDDLE LAYER n = 1.5, k = 0.1
BOTTOM LAYER n = 1.5, k = 0.2

□ 0-1  ▨ 1-2  ▨ 2-3  ▨ 3-4  ■ 4-5      SUBSTRATE REFLECTANCE (%)

BIPHENYL DERIVATIVE, RESIST BOTTOM LAYER MATERIAL, BOTTOM LAYER FORMING METHOD, AND PATTERNING PROCESS

CROSS-REFERENCE TO RELATED APPLICATION

This non-provisional application claims priority under 35 U.S.C. §119(a) on Patent Application No. 2011-069703 filed in Japan on Mar. 28, 2011, the entire contents of which are hereby incorporated by reference.

TECHNICAL FIELD

This invention relates to a resist bottom layer material for forming a resist bottom layer useful as an antireflective coating (ARC) in the multilayer resist process used in micropatterning for the fabrication of semiconductor devices or the like, a method for forming a resist bottom layer, and a pattern forming process adapted for the lithography including exposure to DUV, KrF excimer laser (248 nm), ArF excimer laser (193 nm), $F_2$ laser (157 nm), $Kr_2$ laser (146 nm), $Ar_2$ laser (126 nm), soft X-ray or EUV (13.5 nm), electron beam, or X-ray, using the resist bottom layer material. It also relates to a biphenyl derivative.

BACKGROUND ART

A number of recent efforts are being made to achieve a finer pattern rule in the drive for higher integration densities and operating speeds in LSI devices. The light exposure lithography commonly used in the art is approaching to the essential limit of resolution determined by the light source wavelength.

As the light source used in the lithography for resist pattern formation, g-line (436 nm) or i-line (365 nm) from a mercury lamp has been widely used. One means believed effective for further reducing the feature size is to reduce the wavelength of exposure light. For the mass production process of 64 M-bit DRAM, the exposure light source of i-line (365 nm) was replaced by a KrF excimer laser having a shorter wavelength of 248 nm. However, for the fabrication of DRAM with a degree of integration of 1 G or more requiring a finer patterning technology (processing feature size 0.13 μm or less), a shorter wavelength light source is required. In particular, photolithography using ArF excimer laser light (193 nm) is now under investigation.

On the other hand, it is known in the art that the bilayer resist process is advantageous in forming a high-aspect ratio pattern on a stepped substrate. In order that a bilayer resist film be developable with a common alkaline developer, high molecular weight silicone compounds having hydrophilic groups such as hydroxyl and carboxyl groups must be used.

Among silicone base chemically amplified positive resist compositions, recently proposed were those compositions for KrF excimer laser exposure comprising a base resin in the form of polyhydroxybenzylsilsesquioxane, which is a stable alkali-soluble silicone polymer, in which some phenolic hydroxyl groups are protected with t-BOC groups, in combination with an acid generator (see JP-A H06-118651). For ArF excimer laser exposure, positive resist compositions comprising as a base a silsesquioxane of the type in which cyclohexanecarboxylic acid has substituted thereon an acid labile group were proposed (see JP-A H10-324748). For $F_2$ laser exposure, a positive resist composition based on a silsesquioxane having hexafluoroisopropyl alcohol as a dissolvable group was proposed (see JP-A 2002-55456). The above polymer bears in its backbone a polysilsesquioxane containing a ladder skeleton produced through polycondensation of a trialkoxysilane or trihalosilane.

Silicon-containing (meth)acrylate polymers were proposed as a resist base polymer having silicon pendants on side chains (see JP-A H09-110938).

The lower (or bottom) layer of the bilayer resist process is formed of a hydrocarbon compound which can be etched with oxygen gas, and must have high etch resistance since it serves as a mask when the underlying substrate is subsequently etched. For oxygen gas etching, the bottom layer must be formed solely of a silicon atom-free hydrocarbon. To improve the line-width controllability of the upper (or top) layer of silicon-containing resist and to minimize the sidewall corrugation and pattern collapse by standing waves, the bottom layer must also have the function of an antireflective coating (ARC). Specifically, the reflectance from the resist bottom layer back into the resist top layer must be reduced to or below 1%.

Now, the results of calculation of reflectance at film thickness varying up to the maximum of 500 nm are shown in FIGS. 2 and 3. Assume that the exposure wavelength is 193 nm, and the resist top layer has an n value of 1.74 and a k value of 0.02. FIG. 2 shows substrate reflectance when the resist bottom layer has a fixed k value of 0.3, the n value varies from 1.0 to 2.0 on the ordinate and the film thickness varies from 0 to 500 nm on the abscissa. Assuming that the resist bottom layer of the bilayer resist process has a thickness of 300 nm or greater, optimum values at which the reflectance is reduced to or below 1% exist in the refractive index (n) range of 1.6 to 1.9 which is approximate to or slightly higher than that of the resist top layer.

FIG. 3 shows substrate reflectance when the resist bottom layer has a fixed n value of 1.5 and the k value varies from 0 to 0.8. Assuming that the resist bottom layer of the bilayer resist process has a thickness of at least 300 nm, the reflectance can be reduced to or below 1% as long as the k value is in a range of 0.24 to 0.15. By contrast, the antireflective coating used in the form of a thin film of about 40 nm thick in the single-layer resist process has an optimum k value in the range of 0.4 to 0.5, which differs from the optimum k value of the resist bottom layer used with a thickness of 300 nm or greater in the bilayer resist process. For the resist bottom layer in the bilayer resist process, a film having a lower k value, that is, more transparent is necessary.

As the material for forming a resist bottom layer in 193 nm lithography, copolymers of polyhydroxystyrene with acrylates are under study as described in SPIE Vol. 4345 (2001) p 50. Polyhydroxystyrene has a very strong absorption at 193 nm and its k value is as high as around 0.6 by itself. By copolymerizing it with an acrylate having a k value of almost 0, the k value of the copolymer is adjusted to around 0.25.

However, the resistance of the acrylate to substrate etching is weak as compared with polyhydroxystyrene, and a considerable proportion of the acrylate must be copolymerized in order to reduce the k value. As a result, the resistance to substrate etching is considerably reduced. The etch resistance is not only reflected by the etching speed, but also evidenced by the development of surface roughness after etching. Through copolymerization of acrylate, the surface roughness after etching is increased to a level of serious concern.

Also proposed was a tri-layer process of stacking a resist top layer of a silicon-free single-layer resist film, a resist middle layer containing silicon below the top layer, and a resist bottom layer of organic film below the middle layer. See J. Vac. Sci. Technol., 16(6), November/December 1979. Since the single-layer resist generally provides better resolution than the silicon-bearing resist, the tri-layer process permits such a high resolution single-layer resist to be used as an imaging layer for light exposure. A spin-on-glass (SOG) coating is used as the resist middle layer. A number of SOG films have been proposed.

In the trilayer process, the optimum optical constants of the bottom layer for controlling reflection from the substrate are different from those in the bilayer process. The purpose of minimizing substrate reflection, specifically to a level of 1% or less is the same between the bi- and tri-layer processes. In the bilayer process, only the resist bottom layer is endowed with the antireflective effect. In the tri-layer process, either one or both of the resist middle layer and resist bottom layer may be endowed with the antireflective effect.

U.S. Pat. No. 6,506,497 and U.S. Pat. No. 6,420,088 disclose silicon-containing layer materials endowed with antireflective effect. In general, a multi-layer antireflective coating has greater antireflective effect than a single-layer antireflective coating and is commercially widely used as an antireflective film for optical articles. A higher antireflective effect is obtainable by imparting an antireflective effect to both a resist middle layer and a resist bottom layer. If the silicon-containing resist middle layer in the trilayer process is endowed with the function of ARC, the resist bottom layer need not necessarily possess the maximum function of ARC as in the case of the bilayer process. In the trilayer process, the resist bottom layer is required to have high etch resistance during substrate processing rather than the ARC function. Then a novolak resin containing more aromatic groups and having high etch resistance has been used as the resist bottom layer in the trilayer process.

FIG. 4 illustrates substrate reflectance with a change of the k value of the resist middle layer. It is seen that by setting a k value as low as 0.2 or less and an appropriate thickness to the resist middle layer, a satisfactory antireflective effect as demonstrated by a substrate reflectance of up to 1% is achievable. In general, the ARC film must have a k value of 0.2 or greater in order to reduce reflectance to or below 1% at a film thickness of 100 nm or less (see FIG. 3). In the trilayer resist structure wherein the resist bottom layer serves to restrain reflection to a certain extent, the resist middle layer may have an optimum k value of less than 0.2.

FIGS. 5 and 6 illustrate changes of reflectance with the varying thickness of the resist middle layer and resist bottom layer, when the resist bottom layer has a k value of 0.2 and 0.6, respectively. The resist bottom layer in FIG. 5 has a k value of 0.2 which assumedly corresponds to the resist bottom layer optimized for the bilayer process, and the resist bottom layer in FIG. 6 has a k value of 0.6 which is approximate to the k values at 193 nm of novolak and polyhydroxystyrene. The thickness of the resist bottom layer varies with the topography of the substrate whereas the thickness of the resist middle layer is kept substantially unchanged so that presumably it can be coated to the predetermined thickness.

The resist bottom layer with a higher k value (0.6) is effective in reducing reflectance to 1% or less with a thinner film. In the event that the resist bottom layer has a k value of 0.2 and a thickness of 250 nm, the resist middle layer must be increased in thickness in order to provide a reflectance of 1% or less. Increasing the thickness of the resist middle layer is not preferable because a greater load is applied to the resist film as the uppermost layer during dry etching of the resist middle layer.

FIGS. 5 and 6 illustrate reflection during dry exposure through an exposure tool having a lens with a NA of 0.85, indicating that by optimizing the n and k values and thickness of the resist middle layer for the trilayer process, a reflectance of up to 1% is achievable independent of the k value of the resist bottom layer. Nevertheless, with the advance of the immersion lithography, the NA of the projection lens increases beyond 1.0, and the angles of light entering not only the resist film, but also the underlying ARC film become smaller. The ARC film serves to control reflection due to the absorption of the film itself and the offsetting effect by optical interference. Since oblique light produces a less optical interference effect, reflection increases. Of the films in the trilayer process, it is the resist middle layer that provides reflection control by utilizing the optical interference effect. The resist bottom layer is too thick to utilize the optical interference effect and lacks the anti-reflective function due to the offsetting effect by optical interference. It is necessary to control the reflection from the surface of the resist bottom layer. To this end, the resist bottom layer must have a k value of less than 0.6 and an n value approximate to that of the overlying, resist middle layer. If a film has a too small value of k and too high transparency, reflection from the substrate also occurs, and a k value of about 0.25 to 0.48 is optimum in the case of immersion lithography at NA 1.3. With respect to the n value, a value approximate to the resist's n value of 1.7 is the target for both the middle and bottom layers.

Since benzene ring structure has very strong absorption, cresol novolak resins and polyhydroxystyrene resins containing the same have k values in excess of 0.6. Naphthalene ring structure is one of structures having higher transparency at wavelength 193 nm and higher etch resistance than the benzene ring. For example, JP-A 2002-014474 discloses a resist bottom layer comprising a naphthalene or anthracene ring. According to the inventors' measurements, naphthol co-condensed novolak resin and polyvinylnaphthalene resin have a k value between 0.3 and 0.4. Also the naphthol co-condensed novolak resin and polyvinylnaphthalene resin have a low n value at wavelength 193 nm, specifically, the n value is 1.4 for the naphthol co-condensed novolak resin and as low as 1.2 for the polyvinylnaphthalene resin. Acenaphthylene polymers disclosed in JP-A 2001-040293 and JP-A 2002-214777, for example, have a n value of 1.5 and a k value of 0.4 at 193 nm, close to the target values. There is a need for a bottom layer having a high n value, a low k value, transparency and high etch resistance. Notably JP-A 2010-122656 discloses a resist bottom layer material having a bisnaphthol group, the material having n and k values close to the target values, and improved etch resistance.

If the underlying processable substrate has steps, it is necessary to deposit a resist bottom layer to planarize the steps. By the planarization of the resist bottom layer, a variation in thickness of an overlying film, which may be a resist middle layer or a resist top layer or photoresist film, is minimized, and the focus margin of lithography can be enlarged.

When an amorphous carbon bottom layer is formed by CVD using a reactant gas such as methane, ethane or acetylene gas, it is difficult to bury steps to be flat. On the other hand, when a resist bottom layer is formed by spin coating, there is a benefit that irregularities on the substrate can be buried. Suitable means for improving the burying properties (step coverage) of a coating material include the use of a novolak resin having a low molecular weight and a broad molecular weight distribution as disclosed in JP-A 2002-047430 and a blend of a base polymer and a low molecular weight compound having a low melting point as disclosed in JP-A H11-154638.

It is known from SPIE vol. 469, p 72 (1984) that novolak resins cure through intermolecular crosslinking merely by heating. Reported therein is a crosslinking mechanism by radical coupling that upon heating, a phenoxy radical generates from a phenolic hydroxyl group of cresol novolak resin, and the radical migrates to methylene, a linking group of the novolak resin via resonance, whereby methylene moieties crosslink together. JP 3504247 discloses a pattern forming process using a bottom layer having a carbon density which is increased by thermally induced dehydrogenation or dehydration condensation reaction of polycyclic aromatic compounds such as polyarylene, naphthol novolak, and hydroxyanthracene novolak.

A vitreous carbon film is formed by heating at or above 800° C. (see Glass Carbon Bull. Chem. Soc. JPN, 41 (12) 3023-3024 (1968)). However, the upper limit of the temperature to which the wafer can be heated by the lithography wafer process is up to 600° C., preferably up to 500° C. when thermal impacts like device damage and wafer deformation are taken into account.

It is reported in Proc. of Symp. Dry. Process, p 11 (2005) that as the processing line width is reduced, the resist bottom layer can be twisted or bowed when the processable substrate is etched using the resist bottom layer as mask. Allegedly twisting can be prevented by applying a resist bottom layer having a low hydrogen content. An amorphous carbon film formed by CVD is effective for preventing twist because the hydrogen content of the film can be minimized. However, the CVD has poor step coverage as pointed out above, and the CVD apparatus may be difficult to introduce because of its price and footprint area. If the twist problem can be solved by a bottom layer material from which a film can be formed by coating, specifically spin coating, significant merits would result from simplification of process and apparatus.

Also under study is a multilayer process in which a hard mask is formed on the resist bottom layer by the CVD technique. In the case of silicon-based hard masks (such as silicon oxide, silicon nitride, and silicon oxynitride films) as well, inorganic hard masks formed by CVD or similar deposition techniques have more etch resistance than hard masks formed by the spin coating technique. In the event the processable substrate is a low-dielectric-constant film, the photoresist may be poisoned therefrom (known as substrate poisoning). The CVD film is more effective as a barrier film for preventing the substrate poisoning.

Then a process involving forming a resist bottom layer by spin coating for planarization purpose, and forming an inorganic hard mask middle layer as the resist middle layer by a CVD technique is investigated. When an inorganic hard mask middle layer, especially a nitride film, is formed by a CVD technique, the substrate must be heated at a temperature of at least 300° C., typically about 400° C. Accordingly, when the resist bottom layer is formed by spin coating, the substrate must have heat resistance at 400° C. Ordinary cresol novolak resins, naphthol novolak resins, and even fluorene bisphenol resins known to be heat resistant fail to withstand heat at 400° C., experiencing a substantial film loss after heating. There is a need for a resist bottom layer which can withstand heating at high temperature when an inorganic hard mask middle layer is formed by a CVD technique.

Because of the problem of film loss or resin degradation after heating due to shortage of heat resistance, heat treatment of a resist bottom layer material is usually carried out at or below 300° C., typically 80 to 300° C. The heat treated film, however, still suffers from thickness loss after solvent treatment or twisting of the pattern during etching of the substrate.

As discussed above, it would be desirable to have a method for forming a resist bottom layer which has optimum values of n and k as the ARC film, step coverage, etching resistance, and solvent resistance, and has sufficient heat resistance to withstand high temperature encountered during formation of an inorganic hard mask middle layer by a CVD or similar deposition technique, and prevents pattern twisting during substrate etching.

CITATION LIST

Patent Document 1: JP-A H06-118651
Patent Document 2: JP-A H10-324748
Patent Document 3: JP-A 2002-055456
Patent Document 4: JP-A H09-110938
Patent Document 5: U.S. Pat. No. 6,506,497
Patent Document 6: U.S. Pat. No. 6,420,088
Patent Document 7: JP-A 2002-014474
Patent Document 8: JP-A 2001-040293
Patent Document 9: JP-A 2002-214777
Patent Document 10: JP-A 2010-122656
Patent Document 11: JP-A 2002-047430
Patent Document 12: JP-A H11-154638
Patent Document 13: JP 3504247
Non-Patent Document 1: SPIE Vol. 4345 (2001) p 50
Non-Patent Document 2: J. Vac. Sci. Technol., 16(6), November/December 1979
Non-Patent Document 3: SPIE Vol. 469 (1984) p 72
Non-Patent Document 4: Glass Carbon Bull. Chem. Soc. JPN. 41 (12) 3023-3024 (1968)
Non-Patent Document 5: Proc. of Symp. Dry. Process, 2005, p 11

SUMMARY OF INVENTION

An object of the present invention is to provide a biphenyl derivative; an resist bottom layer material comprising the biphenyl derivative and useful to form a resist bottom layer in a multilayer resist film of at least three layers used in the lithography, the resist bottom layer being capable of reducing reflectance, having etch resistance, heat resistance, and solvent resistance, and being devoid of twist during etching of an underlying substrate; a method for forming a resist bottom layer using the resist bottom layer material; and a pattern-forming process using the resist bottom layer material.

In a first aspect, the invention provides a biphenyl derivative having the general formula (1).

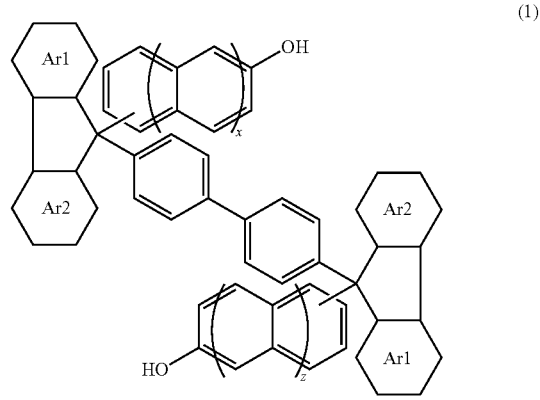

(1)

Herein cyclic structures Ar1 and Ar2 denote a benzene or naphthalene ring, x and z are each independently 0 or 1.

In a second aspect, the invention provides a biphenyl derivative comprising a partial structure having the general formula (2).

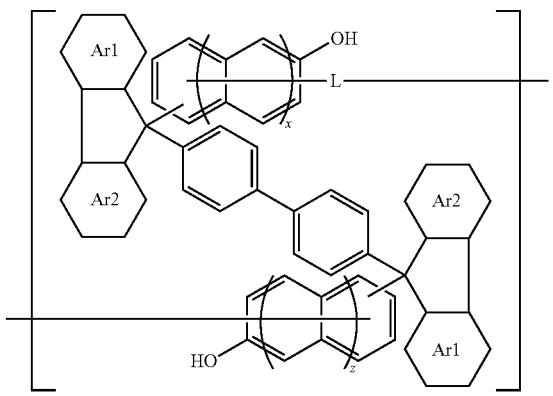

(2)

Herein cyclic structures Ar1 and Ar2 denote a benzene or naphthalene ring, x and z are each independently 0 or 1, and L is a single bond or a $C_1$-$C_{20}$ alkylene group.

In a third aspect, the invention provides a resist bottom layer material comprising (i) a biphenyl derivative having formula (1), (ii) a biphenyl derivative comprising a partial structure having formula (2), or (iii) a polymer comprising recurring units of the biphenyl derivative (ii). The resist bottom layer material may further comprise an organic solvent, a crosslinker and/or an acid generator.

In a fourth aspect, the invention provides a method for forming a resist bottom layer which is included in a multilayer resist film of at least three layers used in the lithography, comprising the steps of coating the resist bottom layer material defined above onto a substrate, and heat treating the coating of resist bottom layer material at a temperature of more than 150° C. to 600° C. for 10 to 600 seconds for curing. Typically, the step of coating the resist bottom layer material onto a substrate is performed by spin coating.

In a still further aspect, the invention provides a process for forming a pattern in a substrate by lithography, comprising at least the steps of forming a resist bottom layer on a substrate by the method defined above, forming a resist middle layer on the resist bottom layer using a silicon-containing resist middle layer material, forming a resist top layer on the resist middle layer using a resist top layer material which is a photoresist composition, exposing a pattern circuit region of the resist top layer to radiation, developing the resist top layer with a developer to form a resist pattern therein, etching the resist middle layer using the resist pattern as an etching mask, etching the resist bottom layer using the resulting resist middle layer pattern as an etching mask, and etching the substrate using the resulting resist bottom layer pattern as an etching mask;

a process for forming a pattern in a substrate by lithography, comprising at least the steps of forming a resist bottom layer on a substrate by the method defined above, forming on the resist bottom layer an inorganic hard mask middle layer which is selected from a silicon oxide film, silicon nitride film, and silicon oxynitride film, forming a resist top layer on the inorganic hard mask middle layer using a resist top layer material which is a photoresist composition, exposing a pattern circuit region of the resist top layer to radiation, developing the resist top layer with a developer to form a resist pattern therein, etching the inorganic hard mask middle layer using the resist pattern as an etching mask, etching the resist bottom layer using the resulting inorganic hard mask middle layer pattern as an etching mask, and etching the substrate using the resulting resist bottom layer pattern as an etching mask; or a process for forming a pattern in a substrate by lithography, comprising at least the steps of forming a resist bottom layer on a substrate by the method defined above, forming on the resist bottom layer an inorganic hard mask middle layer which is selected from a silicon oxide film, silicon nitride film, and silicon oxynitride film, forming an organic ARC film on the inorganic hard mask middle layer, forming a resist top layer on the organic ARC film using a resist top layer material which is a photoresist composition, exposing a pattern circuit region of the resist top layer to radiation, developing the resist top layer with a developer to form a resist pattern therein, etching the organic ARC film and inorganic hard mask middle layer using the resist pattern as an etching mask, etching the resist bottom layer using the resulting inorganic hard mask middle layer pattern as an etching mask, and etching the substrate using the resulting resist bottom layer pattern as an etching mask.

Preferably, the step of forming an inorganic hard mask middle layer is performed by CVD or ALD. Also preferably, the resist top layer material is free of a silicon-containing polymer, and the step of etching the resist bottom layer using the middle layer pattern as an etching mask uses an oxygen or hydrogen-based etchant gas.

ADVANTAGEOUS EFFECTS OF INVENTION

Since the method for forming a resist bottom layer which is included in a multilayer resist film of at least three layers used in the lithography uses a resist bottom layer material comprising a biphenyl derivative having formula (1) or (2) or a polymer comprising recurring units of the biphenyl derivative, the resulting resist bottom layer has values of n and k optimum as ARC film, step coverage, improved etch resistance, high heat resistance and solvent resistance, capable of minimizing outgassing during bake, and being devoid of twist during etching of an underlying substrate through a line pattern having a high aspect ratio and a width of less than 60 nm. When an inorganic hard mask is formed by CVD on the resist bottom layer which has been formed by a spin coating technique, the resist bottom layer has sufficient heat resistance to withstand the temperature treatment for forming the inorganic hard mask middle layer. A pattern forming process utilizing the resist bottom layer formed by spin coating in combination with the inorganic hard mask formed by CVD is available.

Figure 1A:
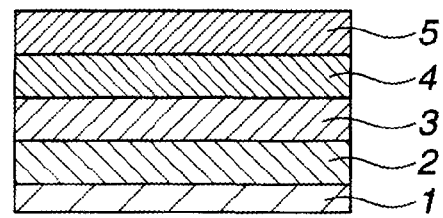
FIG. 1 illustrates a trilayer resist working process, FIGS. 1A through 1F showing steps of stacking and etching three layers.

It is noted that the definition of complex index of refraction includes a refractive index (n) and an extinction coefficient (k).

DESCRIPTION OF THE PREFERRED EMBODIMENTS

In the disclosure, the singular forms "a," an and the include plural referents unless the context clearly dictates otherwise. The notation (Cn-Cm) means a group containing from n to m carbon atoms per group.

The abbreviations and acronyms have the following meaning.

Mw: weight average molecular weight

Mn: number average molecular weight

Mw/Mn: molecular weight distribution or dispersity

GPC: gel permeation chromatography

PEB: post-exposure baking

ARC: antireflective coating

BARC: bottom antireflective coating

It is understood that for some structures represented by chemical formulae which contain asymmetric carbon, there can exist enantiomers and diastereomers. In such a case, a single formula collectively represents all such isomers. The isomers may be used alone or in admixture.

Biphenyl Derivative

In one embodiment of the invention, a biphenyl derivative has the general formula (1).

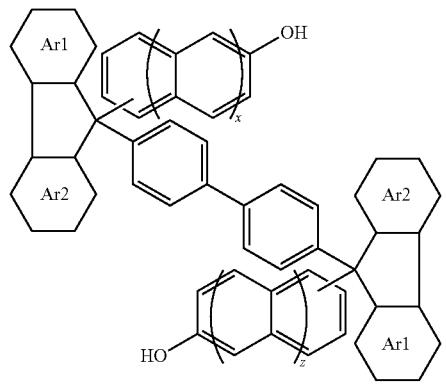

(1)

Herein cyclic structures Ar1 and Ar2 denote a benzene or naphthalene ring, and x and z are each independently 0 or 1.

In formula (1), each of Ar1 and Ar2 denotes a benzene or naphthalene ring. Preferred examples of the partial structure:

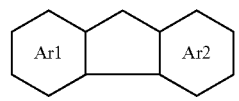

include the following partial structures.

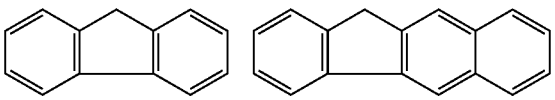

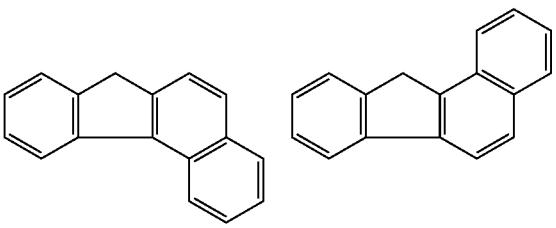

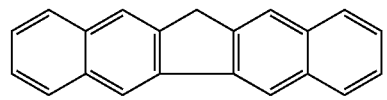

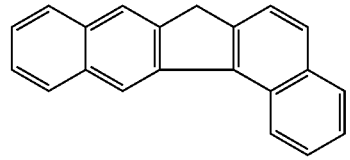

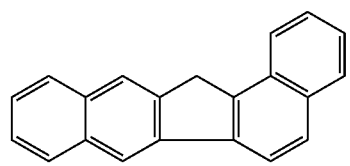

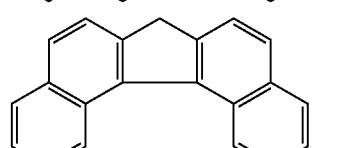

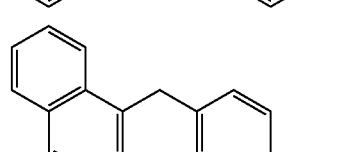

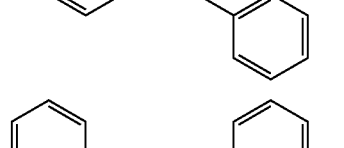

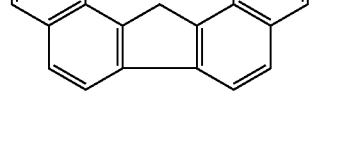

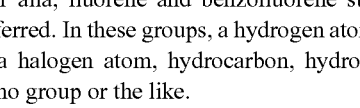

Inter alia, fluorene and benzofluorene structures are more preferred. In these groups, a hydrogen atom may be replaced by a halogen atom, hydrocarbon, hydroxyl, alkoxy, nitro, cyano group or the like.

In formula (1), each of x and z is independently 0 or 1. Preferred examples of the partial structures:

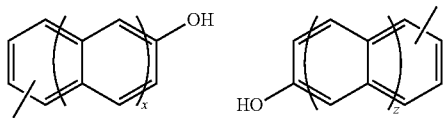

include each independently the following partial structures.

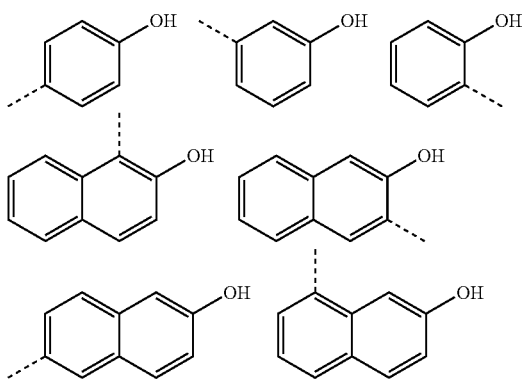

Herein, the broken line denotes a valence bond.

It is described how to prepare the biphenyl derivative having formula (1). One typical method is shown by the reaction scheme below although the method is not limited thereto. Specifically, the biphenyl derivative (1) is prepared by performing addition reaction of an organometallic reagent (4) to a ketone compound (3) to form a compound (5), and reacting compound (5) with phenol or naphthol to form compound (1). Preferably 0.1 to 20 moles, more preferably 0.25 to 0.5 mole of organometallic reagent (4) is used per mole of ketone compound (3).

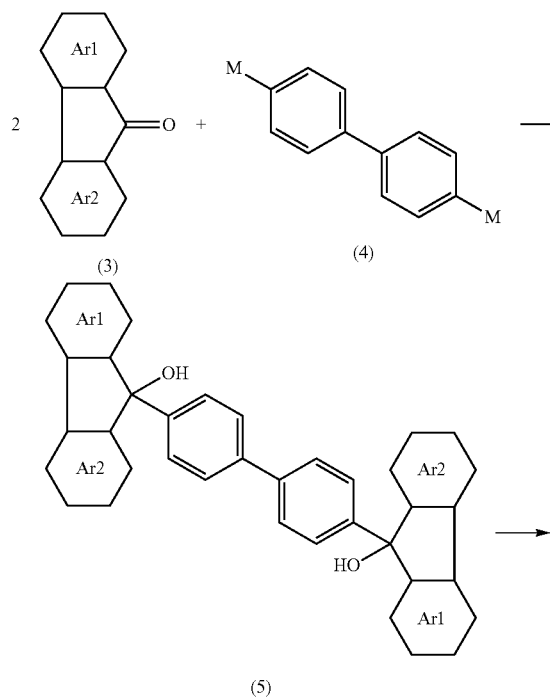

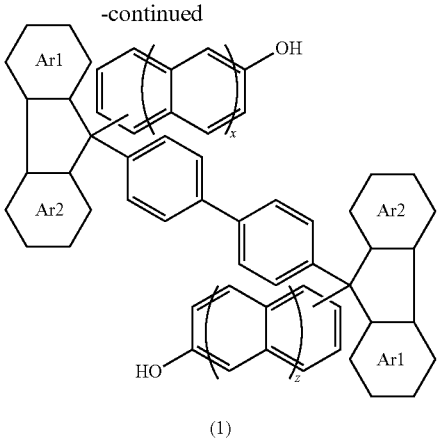

Herein, cyclic structures Ar1 and Ar2 are as defined above, and M is Li or MgX wherein X is a halogen atom.

Exemplary of the organometallic reagent (4) are Grignard reagents, organolithium reagents, organozinc reagents, and organotitanium reagents, with the Grignard reagents and organolithium reagents being preferred. The Grignard reagents and organolithium reagents may be prepared either by direct metallization between 4,4'-dihalobiphenyl and metallic magnesium or lithium, or by metal-halogen exchange reaction between isopropyl magnesium halide and aliphatic organometallic compounds such as methyl lithium or butyl lithium. Also, the organozinc reagents and organotitanium reagents may be prepared from the Grignard reagents or organolithium reagents by reaction thereof with zinc halide, titanium(IV) halide or alkoxytitanium(IV). A metal salt compound may be co-present in the preparation of organometallic reagent (4) and/or the reaction of organometallic reagent (4) with ketone compound (3). Preferred examples of the metal salt compound include cyanides, halides, and perhydrohalic acid salts, and preferred examples include lithium salts such as lithium chloride, lithium bromide, lithium iodide and lithium perhydrochlorite, and copper salts such as copper (I) cyanide, copper(II) cyanide, copper(I) chloride, copper(II) chloride, and dilithium tetrachlorocuprate. The metal salt compound may be added in an amount of 0.01 to 5.0 equivalents, more preferably 0.2 to 2.0 equivalents relative to the organometallic reagent, for increasing the solubility of the organometallic reagent to facilitate preparation thereof, or for adjusting the nucleophilicity or Lewis acidity of the organometallic reagent. Examples of the solvent which can be used in the preparation of organometallic reagent (4) and the reaction thereof with ketone compound (3) includes ethers such as diethyl ether, dibutyl ether, tetrahydrofuran, 1,4-dioxane, and cyclopentyl methyl ether, hydrocarbons such as benzene, toluene, xylene, mesitylene, hexane, heptane, octane, and isooctane, and aprotic polar solvents such as N,N,N',N'-tetramethylethylenediamine, hexamethylphosphoric triamide, and N,N-dimethylformamide, which may be used alone or in admixture. Although the reaction temperature depends the type of ketone compound (3) and organometallic reagent (4) and other reaction conditions, the temperature is generally selected in a range of −70° C. to 150° C., and preferably when organometallic reagent (4) is an organolithium reagent, in a range of −70° C. to 0° C., and when organometallic reagent (4) is a Grignard reagent, under reflux at room temperature to the boiling point of the solvent. The reaction time may be determined by monitoring the reaction process by chromatography or the like until the reaction comes to completion and is generally 30 minutes to 48 hours.

The next step is dehydration condensation reaction of compound (5) with phenol or naphthol, which is generally carried out in a solventless system or in a solvent in the presence of an acid or base catalyst at room temperature or optionally under cooling or heating. Examples of the solvent which can be used herein include alcohols such as methanol, ethanol, isopropyl alcohol, butanol, ethylene glycol, propylene glycol, diethylene glycol, and glycerol; ethers such as ethylene glycol monomethyl ether, propylene glycol monomethyl ether, diethyl ether, dibutyl ether, diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, and isobutyl methyl ketone; esters such as ethyl acetate, n-butyl acetate, and propylene glycol methyl ether acetate (PGMEA); and aprotic polar solvents such as dimethyl sulfoxide, N,N-dimethylformamide, and hexamethylphosphoric triamide, which may be used alone or in admixture of two or more. Examples of the acid catalyst used herein include mineral acids such as hydrochloric acid, hydrobromic acid, sulfuric acid, nitric acid, phosphoric acid, and heteropoly-acid; organic acids such as oxalic acid, trifluoroacetic acid, methanesulfonic acid, benzenesulfonic acid, p-toluenesulfonic acid, and trifluoromethanesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium(IV) ethoxide, titanium(IV) isopropoxide, and titanium(IV) oxide. Examples of the base catalyst used herein include inorganic bases such as sodium hydroxide, potassium hydroxide, barium hydroxide, sodium carbonate, sodium hydrogen carbonate, potassium carbonate, lithium hydride, sodium hydride, potassium hydride, and calcium hydride; alkyl metals such as methyllithium, n-butyl-lithium, methylmagnesium chloride, and ethylmagnesium bromide; alkoxides such as sodium methoxide, sodium ethoxide, and potassium t-butoxide; and organic bases such as triethylamine, diisopropylethylamine, N,N-dimethylaniline, pyridine, and 4-dimethylaminopyridine. The reaction temperature is preferably from −50° C. to near the boiling point of the solvent, more preferably from room temperature to 100° C.

Described below is the design concept of the biphenyl derivative having formula (1). The biphenyl derivative having formula (1) is used to formulate a material for forming a resist bottom layer which is included in a multilayer resist film of at least three layers used in the lithography. As mentioned above, a film having a high carbon atom density and a low hydrogen atom density is necessary to establish the properties required for the resist bottom layer, including etch resistance, heat resistance, and anti-twisting during substrate etching. Then the bottom layer material should desirably have a high carbon atom density and a low hydrogen atom density.

One exemplary naphthalene derivative used in a resist bottom layer for comparison purposes is a 2-naphthol/fluorenone condensate having formula (6) below, also known as bisnaphthol fluorene (referred to as compound (6), hereinafter), as disclosed in JP-A 2007-99741. One known means for converting compound (6) into a high molecular weight compound is novolak formation. A novolak resin formed using formaldehyde is, for example, a resin comprising recurring units having formula (6') (referred to as resin (6'), hereinafter).

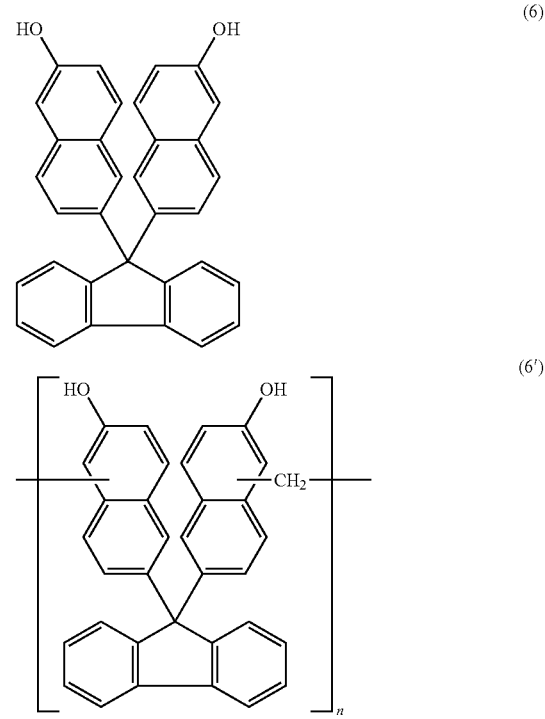

Herein n is a natural number sufficient to provide a molecular weight of 700 to 50,000.

As compared with compound (6) or resin (6'), the biphenyl derivative (1) of the invention has many structural advantages.

[1] While compound (6) always has one fluorene relative to two naphthol structures, biphenyl derivative (1) has two fluorene structures and one biphenyl structure relative to two naphthol or phenol structures. The biphenyl derivative (1) has more aromatic rings, which are effective for etch resistance, than compound (6) by one fluorene structure and one biphenyl structure. Thus biphenyl derivative (1) has a higher carbon density due to the fluorene and biphenyl structures and lower oxygen and hydrogen densities due to dilution of the hydroxyl group of phenol or naphthol.

[2] Compound (6), which is a monomer, must be converted into a high molecular weight compound or polymer by novolak formation or suitable means before it can be used as a bottom layer material. The biphenyl derivative (1) can be used to form a film alone and is ready for use as a resin without a need for further polymerization such as novolak formation.

[3] While novolak form resin (6') has a reduced carbon density (or increased hydrogen density) due to novolak crosslink —$CH_1$—, biphenyl derivative (1) is devoid of such disadvantages because of no need for polymerization.

[4] While a low molecular weight component must be added to novolak resin (6') to improve step coverage (to bury steps), biphenyl derivative (1) can be used alone for good step coverage. Also biphenyl derivative (1) can serve as a low molecular weight component for improving step coverage and be used in combination with another polymer for imparting good etch resistance and step coverage.

[5] While novolak resin (6') having a low molecular weight component added for step coverage improvement gives rise to the problems of outgassing and film loss during hard bake at elevated temperature, biphenyl derivative (1) builds up its molecular weight through self-crosslinking during hard bake at elevated temperature, to become a polymer having high heat resistance, mitigating the outgassing and film loss problems.

[6] If necessary, biphenyl derivative (1) can be converted into a polymer by novolak formation with a polycondensable monomer.

Improved properties of the bottom layer film attributable to these advantages [1] to [6] will be demonstrated in Examples.

For use as the resist bottom layer material, if desired, the present biphenyl derivative (1) may be increased in molecular weight, that is, converted into a (macromolecular) biphenyl derivative comprising a partial structure having the general formula (2).

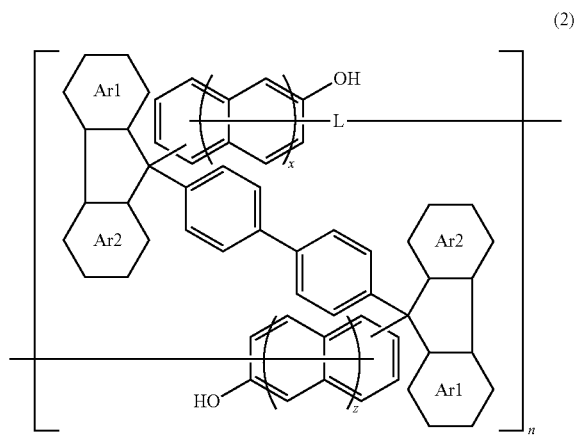

(2)

Herein cyclic structures Ar1 and Ar2 denote a benzene or naphthalene ring, x and z are each independently 0 or 1, L is a single bond or an alkylene group of 1 to 20 carbon atoms, preferably 1 to 15 carbon atoms, and n is such a natural number as to provide a molecular weight of up to 200,000, preferably 700 to 50,000.

In formula (2), the linking group -L- is not limited to one, and a plurality of linking groups may be included. The number of linking groups is preferably 1 to 5, more preferably 1 to 3. When only one linking group -L- is included, a plurality of biphenyl derivative (1) units are linked via the linking group -L- in a linear or one-dimensional array. When a plurality of linking groups -L- are included, a three-dimensional network structure forms wherein a crosslink via -L- is introduced between partial structures in addition to the one-dimensional array.

Accordingly, the macromolecular biphenyl derivative always includes a partial structure having formula (2). The macromolecular biphenyl derivative having a plurality of linking groups -L- may be represented by the formula (2').

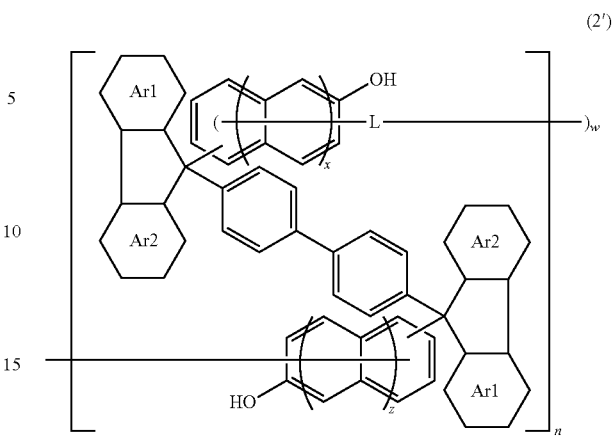

(2')

Herein cyclic structures Ar1 and Ar2 denote a benzene or naphthalene ring, x and z are each independently 0 or 1, L is a single bond or an alkylene group of 1 to 20 carbon atoms, preferably 1 to 15 carbon atoms, w is a natural number, preferably 1 to 5, and more preferably 1 to 3, and n is such a natural number as to provide a molecular weight of up to 200,000, preferably 700 to 50,000.

One exemplary means for converting biphenyl derivative (1) to a higher molecular weight compound is novolak formation through condensation with another component, which is described below. The novolak forming reaction corresponds to formula (2) wherein L is an alkylene group of 1 to 20 carbon atoms. The novolak forming reaction uses an aldehyde, examples of which include formaldehyde, trioxan, paraformaldehyde, acetaldehyde, benzaldehyde, propionaldehyde, phenylacetaldehyde, α-phenylpropionaldehyde, β-phenylpropionaldehyde, 1-naphthaldehyde, 2-naphthaldehyde, and furfural. These aldehyde compounds may be substituted with one or more halogen atom, hydrocarbon, hydroxyl, alkoxy, nitro, cyano group or the like. Of these, formaldehyde and equivalents, benzaldehyde, 1-naphthaldehyde, 2-naphthaldehyde, and substituted forms of the foregoing are preferred. These aldehyde compounds may be used alone or in admixture of two or more. The aldehyde compound may be preferably used in an amount of 0.1 to 5 moles, more preferably 0.3 to 2 moles per mole of biphenyl derivative (1).

The novolak forming reaction may be effected in the presence of a catalyst. Acid catalysts are preferred. Examples of the acid catalyst used herein include mineral acids such as hydrochloric acid, hydrobromic acid, sulfuric acid, nitric acid, phosphoric acid, and heteropoly-acid; organic acids such as oxalic acid, trifluoroacetic acid, methanesulfonic acid, benzenesulfonic acid, p-toluenesulfonic acid, and trifluoromethanesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide. Inter alia, acidic catalysts such as hydrochloric acid, sulfuric acid, nitric acid, formic acid, oxalic acid, acetic acid, methanesulfonic acid, camphorsulfonic acid, p-toluenesulfonic acid, and trifluoromethanesulfonic acid are preferred. The acid catalyst may be used in an amount of $1 \times 10^{-5}$ to $5 \times 10^{-1}$ mole per mole of biphenyl derivative (1). Reaction may be conducted by charging biphenyl derivative (1), aldehyde compound and catalyst all at once, or by adding dropwise any selected component. At the end of reaction, the unreacted reactants, catalyst and the like are removed from the reaction system. To this end, the reactor may be heated to a temperature of 130 to 230° C. under a vacuum of 1 to 50 mmHg for removing any volatiles.

During novolak reaction of biphenyl derivative (1), another phenol compound may be fed for copolymerization. Examples of the phenol compound which can be copolymerized include phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-t-butylphenol, 3-t-butylphenol, 4-t-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-t-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-t-butyl-5-methylphenol, pyrogallol, thymol, isothymol-1-naphthol, 2-naphthol, 2-methyl-1-naphthol, 4-methoxy-1-naphthol, 7-methoxy-2-naphthol, 1,5-dihydroxynaphthalene, 1,6-dihydroxynaphthalene, 1,7-dihydroxynaphthalene, 2,6-dihydroxynaphthalene, 2,7-dihydroxynaphthalene, methyl 3-hydroxynaphthalene-2-carboxylate, 4-tritylphenol, hydroxyanthracene, dihydroxyanthracene, trihydroxyanthracene, hydroxypyrene, bisphenol, and trisphenol. In these compounds, hydrogen may be substituted by halogen, hydrocarbon, hydroxyl, alkoxy, nitro, cyano group or the like.

The present biphenyl derivative (1) may be subjected to polycondensation with a polycondensable monomer to form a polymer, which may be used as the resist bottom layer material. Suitable polycondensable monomers used herein include indene, hydroxyindene, benzofuran, acenaphthylene, biphenyl, dicyclopentadiene, tetrahydroindene, 4-vinylcyclohexene, norbornadiene, 5-vinylnorborn-2-ene, α-pinene, β-pinene, and limonene. In these compounds, hydrogen may be substituted by halogen, hydrocarbon, hydroxyl, alkoxy, nitro, cyano group or the like. Ternary or multi-component copolymers may be used as well. The amount of the other phenol compound or polycondensable monomer used is preferably from more than 0% by weight to 50% by weight based on the weight of the biphenyl derivative.

The novolak resin or polycondensed resin preferably has a Mw of 1,000 to 200,000, more preferably 2,000 to 50,000, as measured versus polystyrene standards by gel permeation chromatography (GPC) using tetrahydrofuran as solvent, and a dispersity (Mw/Mn) in the range of 1.2 to 7. It is preferred that the molecular weight distribution of the resin is narrowed by cutting off the monomeric and oligomeric components and low-molecular weight fractions having a Mw of less than 1,000, because the crosslinking efficiency is increased and the content of volatile components during bake is minimized to prevent contamination around the bake cup.

Another exemplary means for converting biphenyl derivative (1) to a macromolecular one is oxidative coupling reaction by dehydrogenation. The oxidative coupling reaction corresponds to formula (2) wherein w=1 and L is a single bond. Oxidative coupling reaction is performed by heating at a temperature of 80 to 500° C. in the presence of air or oxygen. The catalyst or reactant which can be used herein may be selected from metal salts and complexes such as lead tetraacetate, diacetoxyiodobenzene, vanadium oxychloride, vanadium oxyfluoride, iron(III) chloride, iron(III) perchlorate, potassium hexacyanoferrate(III), ruthenium oxide, cobalt fluoride, thallium trifluoroacetate, copper(II) chloride, and di-μ-hydroxo-(N,N,N',N'-tetramethylethylenediamine) copper(II) chloride. While oxidative coupling reaction may be used as the means for previously converting biphenyl derivative (1) to a macromolecular one, oxidative coupling reaction may be induced by heating in air during film formation. The biphenyl derivative or resin obtained from oxidative coupling reaction may have a molecular weight in the same range as the novolak resin and polycondensed resin described above.

Also, in the biphenyl derivative having formula (1) or (2) or the polymer comprising a biphenyl derivative having formula (2) as some recurring units, a fused aromatic or alicyclic substituent group may be introduced. The substituent group which can be introduced herein is as exemplified below.

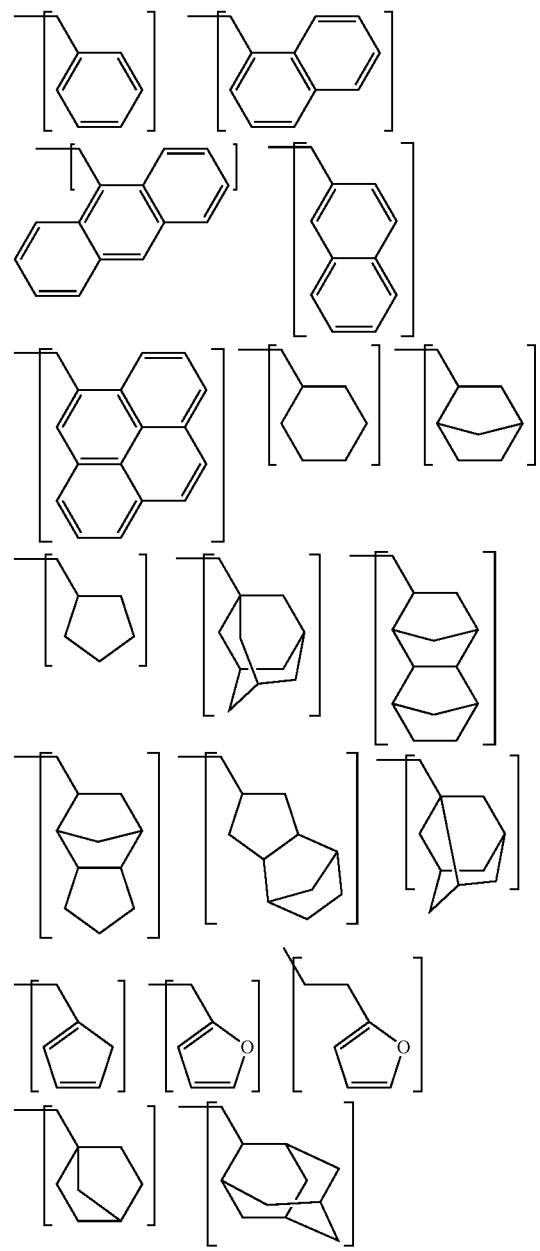

-continued

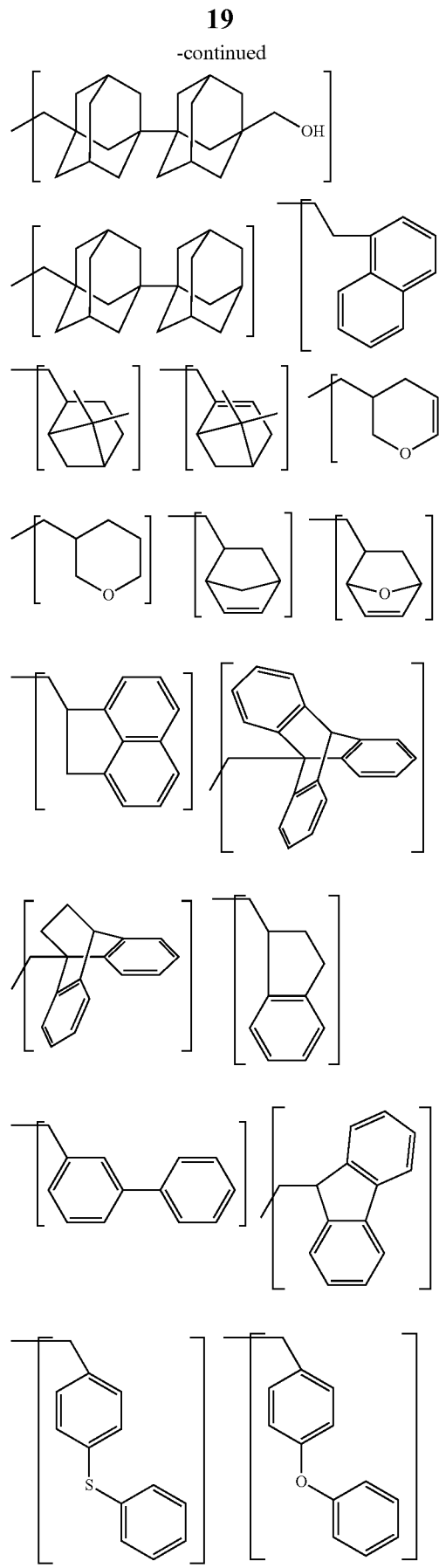

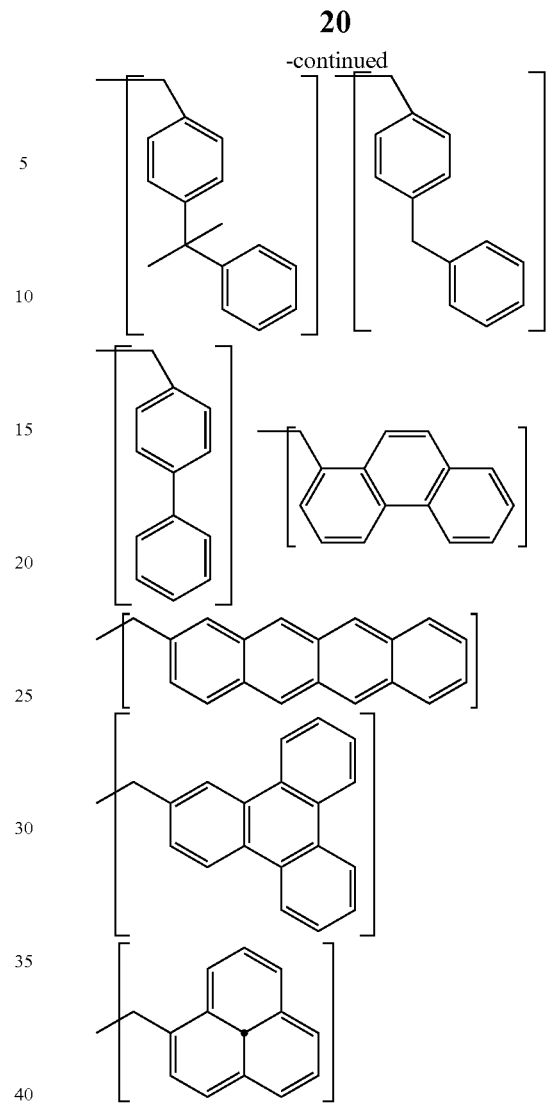

Of these, polycyclic aromatic groups such as anthracenemethyl and pyrenemethyl are most preferred for exposure at 248 nm. A substituent group having an alicyclic structure or naphthalene structure is preferably used for improved transparency at 193 nm. The method of introducing the substituent group may be by reacting an alcohol compound having a hydroxyl group as the site where the substituent group is attached with the biphenyl derivative having formula (1) or (2) or the polymer comprising a biphenyl derivative having formula (2) as some recurring units in the presence of an acid catalyst. Suitable acid catalysts are as exemplified above for the novolak forming reaction. Introduction of a substituent group may be conducted concurrently with the novolak forming reaction.

The biphenyl derivative having formula (1) or (2) or the polymer comprising the same as some recurring units (generally referred to as "inventive compound," hereinafter) may be used as a resist bottom layer material in the method for forming a resist bottom layer in the trilayer process. These inventive compounds have very high heat resistance because of inclusion of quaternary carbon and a carbon density which is as high as approximately 90%. When a hard mask in the form of a silicon oxide, silicon nitride or silicon oxynitride film is formed on the resist bottom layer by CVD or similar deposition technique, a high temperature, specifically a temperature above 300° C. in the case of nitride film is necessary, and the resist bottom layer is thus required to have high heat resistance. Since the inventive compounds are benzene ring fused hydrocarbons, they exhibit relatively low absorption at wavelength 193 nm due to an absorption shift, and are expected to exert better antireflective effect at a film thickness of at least 100 nm when used in the trilayer process. Also, the inventive compounds have higher resistance against $CF_4$/$CHF_3$ gas and $Cl_2$/$BCl_3$ gas etching used in substrate processing than ordinary m-cresol novolak resins. Since the count of hydrogen and oxygen atoms becomes smaller by an increment of the aromatic count, the occurrence of pattern twist during substrate etching is suppressed. By baking at a temperature in excess of 300° C., the bottom layer is endowed with more etch resistance and solvent resistance and the occurrence of pattern twist during substrate etching is suppressed.

Bottom Layer Material

The resist bottom layer material used in the method for forming a resist bottom layer in the trilayer process is defined as comprising (A) the biphenyl derivative having formula (1) or (2) or the polymer comprising the same as some recurring units, as an essential component and preferably (B) an organic solvent. If it is desired to improve spin coating properties and step coverage (to bury substrate steps) as well as the rigidity and solvent resistance of the film, the material may further comprise (C) a blending compound or polymer, (D) a crosslinker, and (E) an acid generator.

The organic solvent (B) used in the bottom layer material may be any desired one as long as components (A) to (E) and other components are dissolvable therein. Suitable solvents which can be added are described in U.S. Pat. No. 7,745,104 (JP-A 2008-065303, paragraphs [0120] and [0121]). Examples of the solvent include, but are not limited to, ketones such as cyclohexanone and methyl-2-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in admixture.

Preferably the solvent is used in an amount of 200 to 10,000 parts, more preferably 300 to 5,000 parts by weight per 100 parts by weight of component (A).

In a preferred embodiment, the resist bottom layer material comprises organic solvent (B), and in a more preferred embodiment, the material further comprises crosslinker (D) and acid generator (E) if it is desired to improve spin coating properties and step coverage as well as the rigidity and solvent resistance of the film.

Optionally, another polymer or compound (C) may be blended in the resist bottom layer material. When the blending compound or polymer is blended with the biphenyl derivative having formula (1) or (2) or the polymer comprising the same as some recurring units, it can serve the functions of improving film formation by spin coating and step coverage. More preferably a choice may be made of polymers having a high carbon density and etching resistance. Suitable blending polymers include novolak resins derived from phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-t-butylphenol, 3-t-butylphenol, 4-t-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-t-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-t-butyl-5-methylphenol, pyrogallol, thymol, isothymol, 4,4'-(9H-fluoren-9-ylidene)bisphenol, 2,2'-dimethyl-4,4'-(9H-fluoren-9-ylidene)bisphenol, 2,2'-diallyl-4,4'-(9H-fluoren-9-ylidene) bisphenol, 2,2'-difluoro-4,4'-(9H-fluoren-9-ylidene) bisphenol, 2,2'-diphenyl-4,4'-(9H-fluoren-9-ylidene) bisphenol, 2,2'-dimethoxy-4,4'-(9H-fluoren-9-ylidene) bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1-naphthol, 2-naphthol, 2-methyl-1-naphthol, 4-methoxy-1-naphthol, 7-methoxy-2-naphthol, and dihydroxynaphthalenes such as 1,5-dihydroxynaphthalene, 1,7-dihydroxynaphthalene and 2,6-dihydroxynaphthalene, methyl 3-hydroxy-naphthalene-2-carboxylate, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborn-2-ene, α-pinene, β-pinene, limonene, etc.; and polyhydroxystyrene, polystyrene, polyvinyl naphthalene, polyvinyl anthracene, polyvinyl carbazole, polyindene, polyacenaphthylene, polynorbornene, polycyclodecene, polytetracyclododecene, polynortricyclene, poly(meth)acrylate, and copolymers thereof. Also included are naphthol-dicyclopentadiene copolymers as described in JP-A 2004-205685, fluorene bisphenol novolak resins as described in JP-A 2005-128509, acenaphthylene copolymers as described in JP-A 2005-250434, phenol-containing fullerene as described in JP-A 2006-227391, bisphenol compounds and novolak resins thereof as described in JP-A 2006-293298, novolak resins of adamantane phenol compounds as described in JP-A 2006-285095, bisnaphthol compounds and novolak resins thereof as described in JP-A 2010-122656; naphthalene resins obtained from dehydration condensation between fluorene or benzofluorene and dinaphthyl ether as represented by the general formula (7):

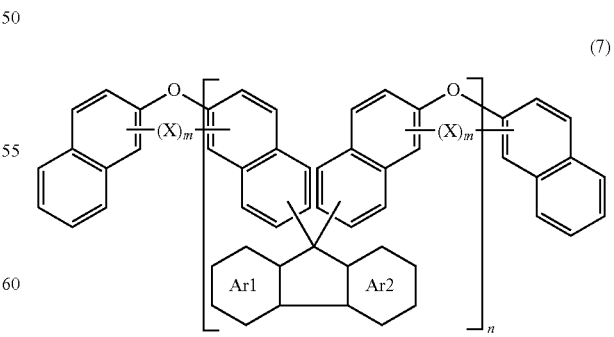

(7)

wherein cyclic structures Ar1 and Ar2 denote a benzene or naphthalene ring, X is a single bond or $C_1$-$C_{20}$ alkylene, m is 0 or 1, and n is such a natural number as to provide a molecular weight of up to 100,000, preferably 700 to 50,000; naphthalene resins obtained from dehydration condensation between fluorene or benzofluorene and 1,1'-bi-2-naphthol as represented by the general formula (8):

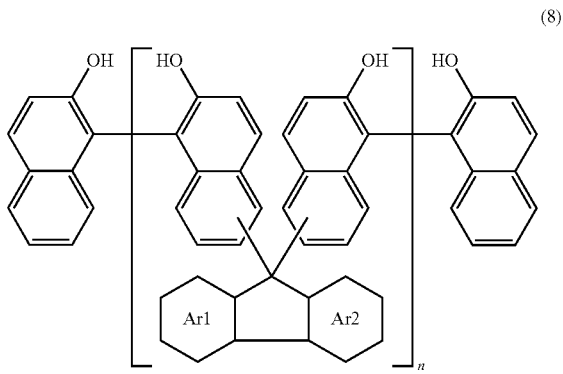

(8)

wherein cyclic structures Ar1 and Ar2 denote a benzene or naphthalene ring, and n is such a natural number as to provide a weight average molecular weight of up to 100,000, preferably 700 to 50,000, as measured by GPC versus polystyrene standards; and fullerene resins as described in JP-A 2008-158002.

The amount of the blending compound or polymer compounded is usually 0 to 1,000 parts by weight, preferably 0 to 500 parts by weight per 100 parts by weight of the biphenyl derivative having formula (1) or (2) or the polymer comprising the same.

Some of the functions required for the resist bottom layer additionally having an antireflective function are the elimination of intermixing with the overlying films (i.e., silicon-containing resist middle layer and resist top layer) and the elimination of diffusion of low molecular weight components into the overlying films (see Proc. SPIE Vol. 2195, p 225-229 (1994)). One common means for preventing intermixing and diffusion is by baking an antireflective film as spin coated for inducing thermal crosslinkage. Then, in the event the antireflective film material contains a crosslinker, a method of introducing crosslinkable substituent groups into the polymer may be employed. Even when a particular crosslinker is not added, the biphenyl derivative having formula (1) or (2) or the polymer comprising the same undergoes crosslinkage through the reaction mechanism (to be described later) by heating at a temperature in excess of 350° C.

Since the biphenyl derivative having formula (1) or (2) or the polymer comprising the same as some recurring units has very high heat resistance, it undergoes substantially no pyrolysis even when baked at a high temperature in excess of 350° C. Since baking at a temperature in excess of 350° C. promotes evaporation of the solvent, the film of the inventive compound tends to increase its carbon density and denseness, exhibiting more etch resistance. In addition, baking at a temperature in excess of 350° C. endows the film with more solvent resistance and prevents the film from being twisted during substrate etching. When a less heat resistant material film is baked at a high temperature in excess of 350° C., the film does not always increase its carbon density, because of possible pyrolysis, and may be degraded in some cases. When the crosslinker and acid generator are added, a higher carbon density and higher denseness are available from baking at a temperature of at least 150° C., preferably 200° C. to 350° C.

Suitable crosslinkers which can be used herein are described in JP-A 2008-065303, paragraphs [0075] to [0080]. Exemplary crosslinkers include melamine compounds, guanamine compounds, glycoluril compounds and urea compounds having substituted thereon at least one group selected from among methylol, alkoxymethyl and acyloxymethyl groups, epoxy compounds, thioepoxy compounds, isocyanate compounds, azide compounds, and compounds having a double bond such as an alkenyl ether group. These compounds may be used as an additive or introduced into a polymer side chain as a pendant. Hydroxy-containing compounds may also be used as the crosslinker. An amount of the crosslinker blended is 0 to 50 parts, preferably 3 to 50 parts by weight per 100 parts by weight of component (A).

An acid generator may be added to the resist bottom layer material to further accelerate the thermally induced crosslinking reaction. Acid generators include those which generate an acid through pyrolysis and those which generate an acid upon exposure to light, and both are useful. The acid generators used herein include those described in JP-A 2008-065303, paragraphs [0081] to [0111]. Exemplary acid generators include onium salts, diazomethane derivatives, glyoxime derivatives, bissulfone derivatives, esters of N-hydroxyimide compounds with sulfonic acids, β-ketosulfonic acid derivatives, disulfone derivatives, nitrobenzylsulfonate derivatives, and sulfonic acid ester derivatives. An amount of the acid generator blended is 0 to 50 parts, preferably 0.1 to 50 parts by weight per 100 parts by weight of component (A).

In the resist bottom layer material, a basic compound may be compounded for improving the storage stability. The basic compound plays the role of an acid quencher for preventing a minute amount of an acid generated by the acid generator from facilitating crosslinking reaction. The basic compound which can be added herein may be any of the compounds described in JP-A 2008-065303, paragraphs [0112] to [0119]. Suitable basic compounds include primary, secondary and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, and imide derivatives. An amount of the basic compound blended is 0 to 2 parts, preferably 0.001 to 2 parts by weight per 100 parts by weight of component (A).

A surfactant may be added to the resist bottom layer material for improving the applicability by spin coating. Suitable surfactants are described in U.S. Pat. No. 7,537,880 (JP-A 2008-111103, paragraphs [0165] to [0166]).

Process

It is now described how to form a pattern using the resist bottom layer material of the invention.

Like photoresists, the resist bottom layer material of the invention can be applied onto a processable substrate by any desired technique such as spin coating, to form a bottom layer thereon. Spin coating and other coating techniques are effective for step coverage. After spin coating, the coating is desirably baked in order to evaporate off the solvent and to promote crosslinking reaction for preventing the bottom layer from intermixing with the resist middle layer and top layer to be subsequently applied thereon. The bake is preferably effected at a temperature of more than 150° C. to 600° C., more preferably 200° C. to 400° C. for a time of 10 to 600 seconds, more preferably 10 to 300 seconds. With thermal impacts such as device damages and wafer deformation taken into account, the upper limit of permissible heating temperature in the lithographic wafer process is up to 600° C., preferably up to 500° C.

As understood from SPIE Vol. 469, p 72 (1984), cited above, when the biphenyl derivative having formula (1) or (2) or the polymer comprising the same used in the method for forming a resist bottom layer according to the invention is heated, radicals are created, helping crosslinking reaction take place. Particularly when the polymer comprising the biphenyl derivative having formula (2) as some recurring units contains a methylene or methine group at the benzyl site, benzyl radicals bond with each other, facilitating crosslinking reaction. Since this reaction is a radical reaction in which no molecules are eliminated, the material film does not undergo shrinkage due to crosslinking as long as the material is fully heat resistant.

Although the bake atmosphere may be air, it is sometimes preferred to introduce an inert gas such as $N_2$, Ar or He into the atmosphere for reducing the oxygen content for the purpose of preventing the resist bottom layer from oxidation. Where it is necessary to control the oxygen concentration for preventing oxidation, the oxygen concentration is preferably up to 1,000 ppm, more preferably up to 100 ppm. It is preferred to prevent the resist bottom layer from oxidation during bake because oxidation can cause an increase of absorption or a drop of etch resistance. On the other hand, bake in air or oxygen-rich gas is sometimes preferable when molecular crosslinking by oxidative coupling is intended.

The thickness of the resist bottom layer may be suitably determined although it is preferably in the range of 30 to 20,000 nm, especially 50 to 15,000 nm. After the resist bottom layer is formed, a silicon-containing resist middle layer and a silicon-free resist top layer are formed thereon in the case of the trilayer process.

According to the process of the invention, a pattern is formed by coating a substrate with the resist bottom layer material comprising the biphenyl derivative having formula (1) or (2) or the polymer comprising the same as some recurring units to form a resist bottom layer thereon, forming a resist top layer of a photoresist composition on the resist bottom layer via an intervening resist middle layer, exposing a predetermined region of the resist top layer to radiation or the like, developing the resist top layer with a developer to form a resist pattern, etching the resist middle layer using the resist pattern as mask, and etching the resist bottom layer and the substrate using the resulting resist middle layer pattern as mask.

In the embodiment wherein the inorganic hard mask middle layer is formed on the resist bottom layer, a silicon oxide film, silicon nitride film or silicon oxynitride (SiON) film is formed by chemical vapor deposition (CVD) or atomic layer deposition (ALD). The formation of nitride film is described in JP-A 2002-334869 and WO 2004/066377. The inorganic hard mask typically has a thickness of 5 to 200 nm, preferably 10 to 100 nm. The most preferred inorganic hard mask is a SiON film which is fully effective as an ARC. Since the substrate reaches a temperature of 300 to 500° C. during deposition of a SiON film, the bottom layer must withstand a temperature of 300 to 500° C. Since the resist bottom layer material comprising the biphenyl derivative having formula (1) or (2) or the polymer comprising the same as some recurring units has heat resistance sufficient to withstand a temperature of 300 to 500° C., it is possible to combine a resist bottom layer formed by spin coating with an inorganic hard mask formed by CVD or ALD.

In one embodiment, a photoresist film is formed on the resist middle layer as the resist top layer. In another embodiment, an organic antireflective coating film (BARC) is formed on the resist middle layer by spin coating, and a photoresist film formed thereon. Where the resist middle layer is a SiON film, an antireflective film consisting of two layers, SiON and BARC films functions to suppress reflection even in the immersion lithography with a high NA in excess of 1.0. Another advantage arising from formation of BARC is to reduce footing of the photoresist pattern immediately above SiON. It is noted that the BARC film is preferably made of common BARC materials used in the general ArF lithography, for example, ARC-29A and ARC-93 from Nissan Chemical Industries, Ltd. and AR-40 from Rohm & Haas. The BARC film preferably has a thickness of 300 to 1,000 angstroms (Å).

Also preferred as the silicon-containing resist middle layer in the trilayer process is a middle layer based on polysilsesquioxane. Reflection may be suppressed by endowing the resist middle layer with the ARC function. Suitable silsesquioxane-based silicon compounds are described, for example, in JP-A 2004-310019, 2007-302873, and 2009-126940. Particularly for 193 nm exposure, when an aromatic rich material having high resistance to substrate etching is used as the resist bottom layer, that resist bottom layer has a high value of k and allows high substrate reflection. However, if reflection can be suppressed by the resist middle layer, then totally the substrate reflection can be suppressed to or below 0.5%. Preferred as the resist middle layer capable of suppressing reflection is anthracene for the 248 nm and 157 nm exposures, or polysilsesquioxane having a pendant in the form of a phenyl or photo-absorptive group having a silicon-silicon bond and capable of acid or heat-induced crosslinking for the 193 nm exposure. The resist middle layer preferably has a thickness of 20 to 100 nm.

For forming the silicon-containing resist middle layer, spin coating is simple and cost effective as compared with CVD.

The resist top layer in the trilayer resist film may be either positive or negative and may be any of commonly used photoresist compositions. When the photoresist composition is applied to form a single-layer resist top layer, a spin coating technique is preferably used as in the case of the resist bottom layer. The photoresist composition is spin coated and then pre-baked, preferably at 60 to 180° C. for 10 to 300 seconds. Thereafter, the resist layer is routinely exposed to radiation through a desired pattern, baked (PEB) and developed with a developer, obtaining a resist pattern. The thickness of the resist top layer is preferably in a range of 30 to 500 nm, more preferably 50 to 400 nm, though not particularly limited. The radiation for exposure may be selected from among high-energy radiation having a wavelength of up to 300 nm, specifically excimer laser beams of 248 nm, 193 nm and 157 nm, soft X-ray (EUV) of 3 to 20 nm, electron beam (EB), and X-ray.

Next, etching is carried out using the resist pattern as mask. In the trilayer process, the resist middle layer, specifically inorganic hard mask is etched with fluorocarbon-base gas using the resist pattern as mask. Then the resist bottom layer is etched with oxygen or hydrogen gas using the resist middle layer pattern, specifically inorganic hard mask pattern as mask.

Next, the processable substrate is etched by a standard technique. For example, when the substrate is $SiO_2$, SiN or silica-base low-dielectric-constant insulating film, etching with a fluorocarbon-base gas is employed. When the substrate is p-Si, Al or W, etching with a chlorine or bromine-base gas is employed. When the substrate processing is etching with a fluorocarbon-base gas, the silicon-containing middle layer in the trilayer process is stripped at the same time as the substrate processing. When the substrate is etched with a chlorine or bromine-base gas, the silicon-containing middle layer must be subsequently stripped by dry etching with a fluorocarbon-base gas after the substrate processing.

The resist bottom layer formed by the inventive method is characterized by resistance to etching of the processable substrate. The processable substrate may be a substrate having a processable layer deposited thereon. The substrate includes those of Si, α-Si, p-Si, $SiO_2$, SiN, SiON, W, TiN, Al and the like, and a suitable material different from the processable layer is selected among them. The processable layer is selected from low-k films of Si, $SiO_2$, SiON, SiN, p-Si, α-Si, W, W—Si, Al, Cu, Al—Si, and the like and stop films thereof, and typically has a thickness of 50 to 10,000 nm, especially 100 to 5,000 nm.

Figure 1B:
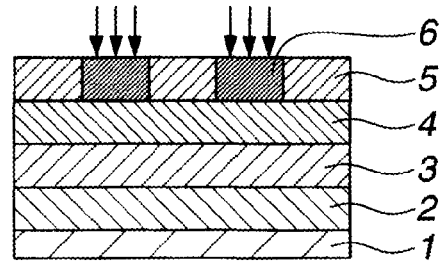
Figure 1C:
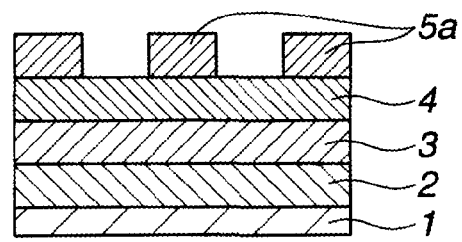
Figure 1D:
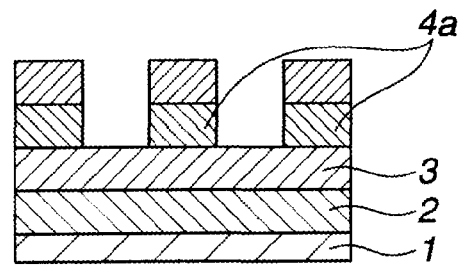
Figure 1E:
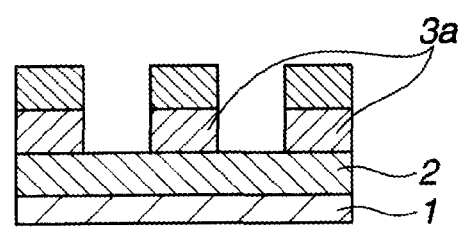
Figure 1F:
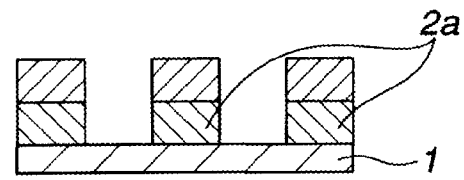
Figure 2:
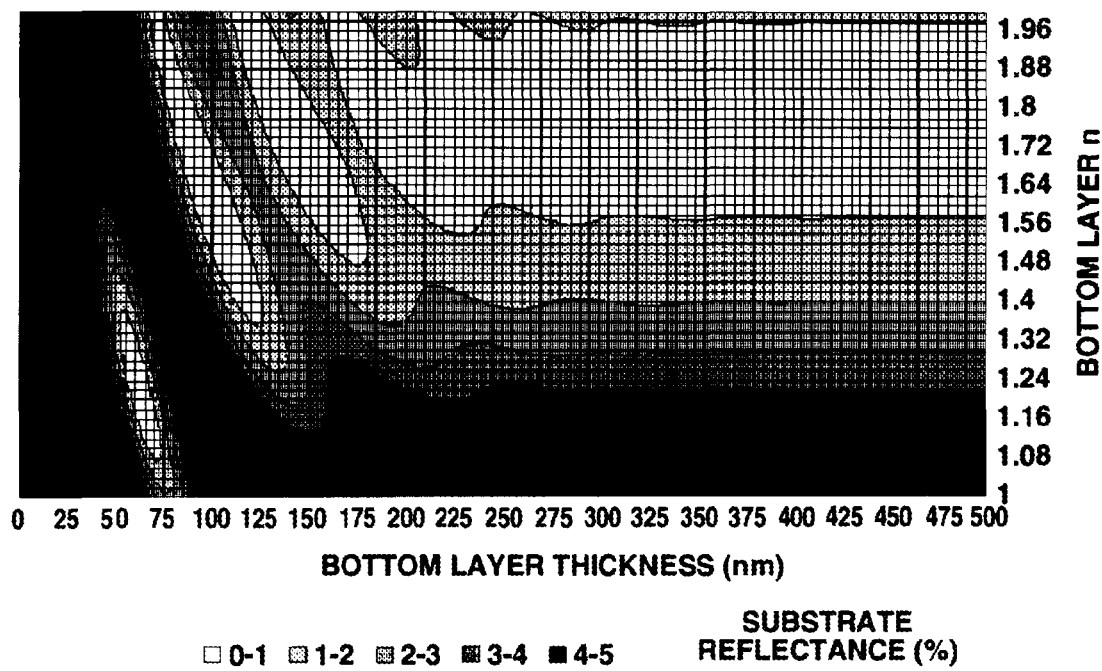
FIG. 2 is a graph plotting the substrate reflectance versus bottom layer thickness in bilayer process when the k value of the bottom layer is fixed at 0.3 and the n value varies from 1.0 to 2.0.
Figure 3:
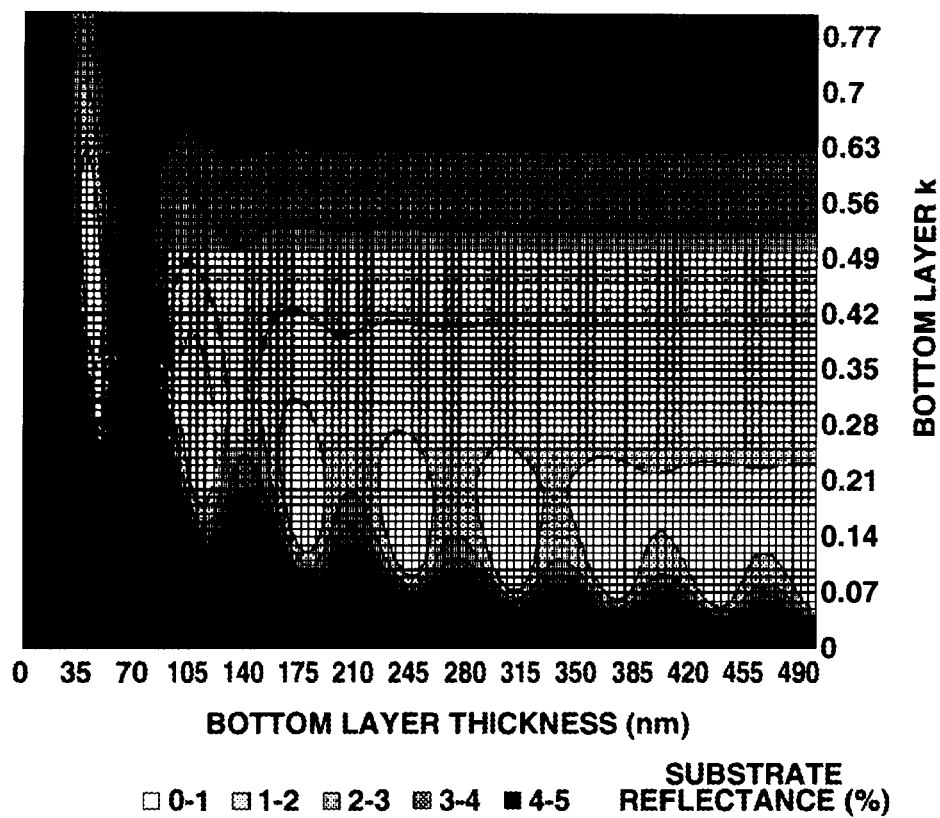
FIG. 3 is a graph plotting the substrate reflectance versus bottom layer thickness in bilayer process when the n value of the bottom layer is fixed at 1.5 and the k value varies from 0 to 0.8.
Figure 4:
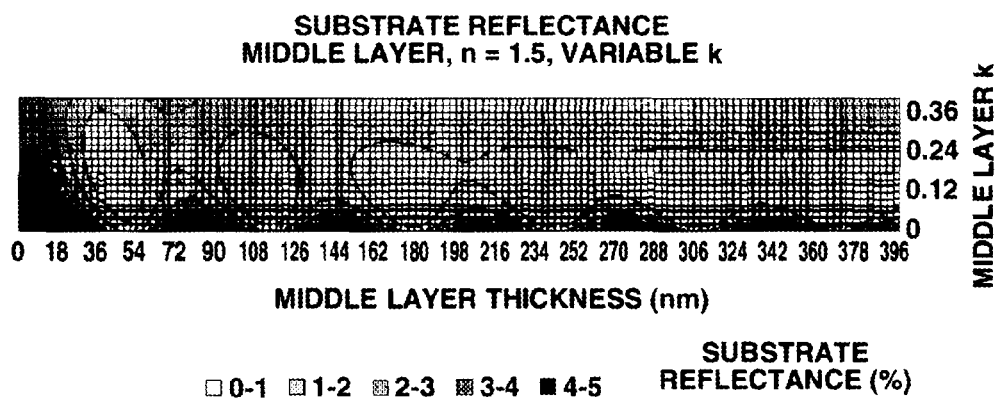
FIG. 4 is a graph plotting the substrate reflectance in trilayer process when the bottom layer has a fixed n of 1.5, a fixed k of 0.6 and a fixed thickness of 500 nm, and the middle layer has a fixed n of 1.5, a k value varying from 0 to 0.3 and a thickness varying from 0 to 400 nm.
Figure 5:
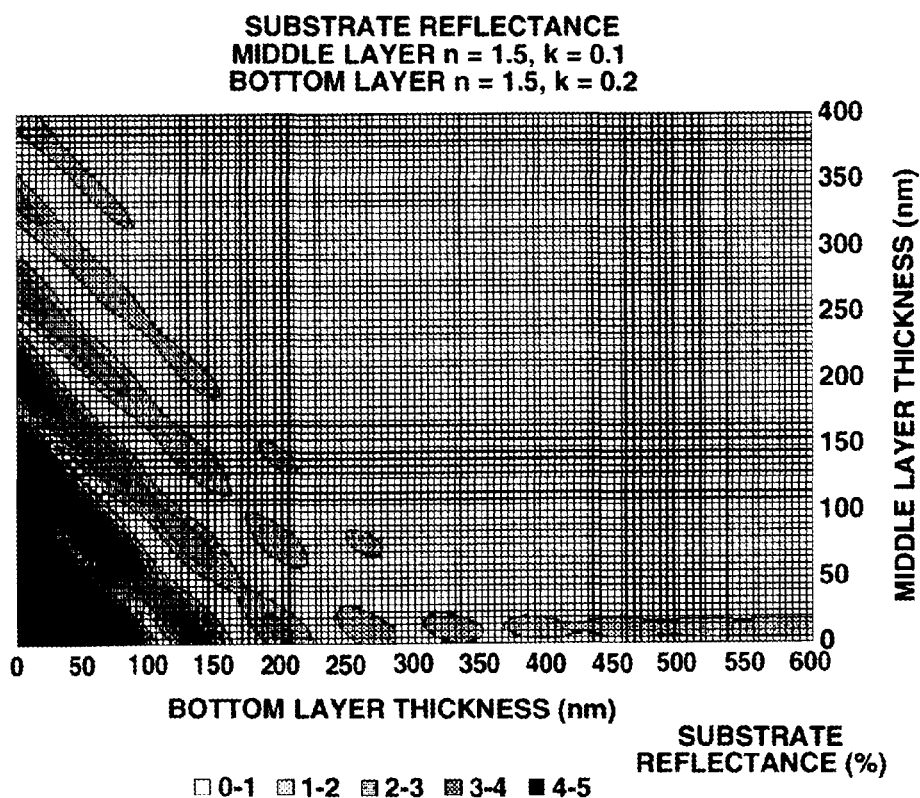
FIG. 5 is a graph plotting the substrate reflectance versus varying thickness of the bottom layer and middle layer in trilayer process when the bottom layer has a fixed n of 1.5 and a fixed k of 0.2, and the middle layer has a fixed n of 1.5 and a fixed k of 0.1.
Figure 6:
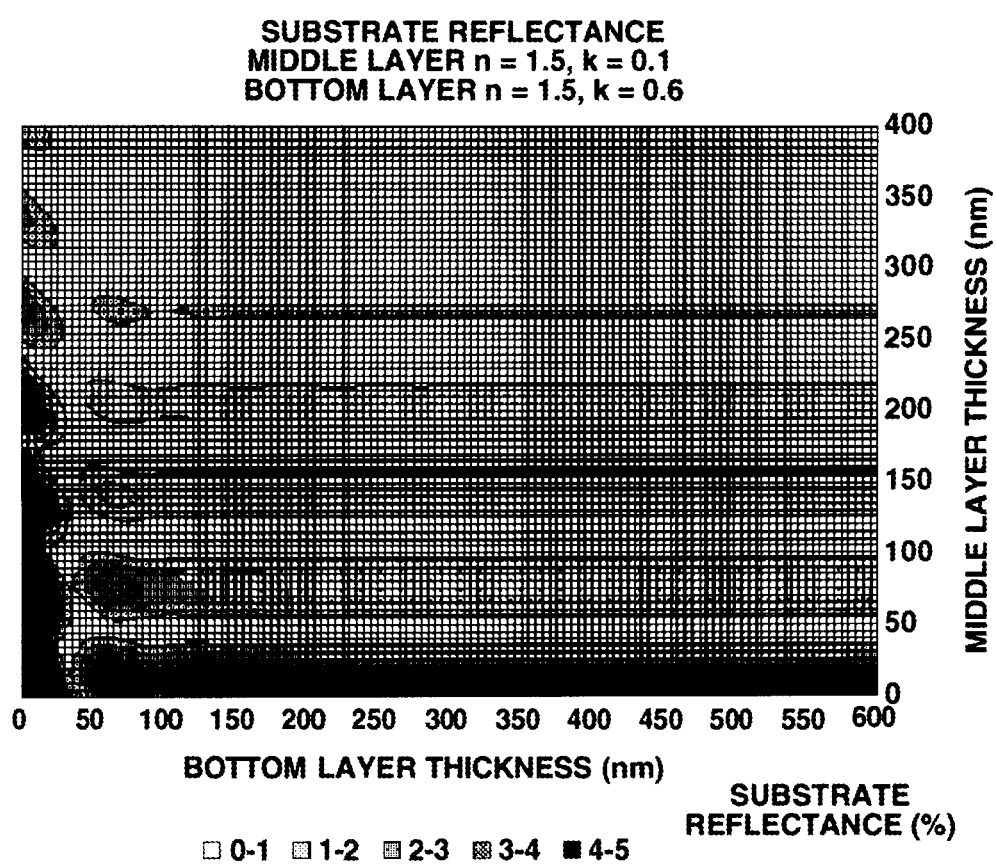
FIG. 6 is a graph plotting the substrate reflectance versus varying thickness of the bottom layer and middle layer in trilayer process when the bottom layer has a fixed n of 1.5 and a fixed k of 0.6, and the middle layer has a fixed n of 1.5 and a fixed k of 0.1.

Referring to FIG. 1, the trilayer resist working process is described. A resist bottom layer 3 is formed on a processable layer 2 lying on a substrate 1, a resist middle layer 4 is formed on the bottom layer 3, and a resist top layer 5 is formed thereon (FIG. 1A). Then a predetermined region 6 of the resist top layer is exposed to radiation (FIG. 1B), PEB, and developed, forming a resist pattern 5a (FIG. 1C). The resist middle layer 4 is etched with CF gas through the resist pattern 5a as mask, forming a resist middle layer pattern 4a (FIG. 1D). The resist pattern 5a is removed, and the resist bottom layer 3 is etched with oxygen plasma through the resist middle layer pattern 4a as mask, forming a resist bottom layer pattern 3a (FIG. 1E). The resist middle layer pattern 4a is removed, and the processable layer 2 is etched through the resist bottom layer pattern 3a as mask, forming a pattern 2a on the substrate 1 (FIG. 1F).

In the embodiment using an inorganic hard mask middle layer, the resist middle layer 4 is the inorganic hard mask middle layer. In the other embodiment using BARC, a BARC layer intervenes between the resist middle layer 4 and the resist top layer 5. Etching of BARC may be continuously followed by etching of the resist middle layer 4. Alternatively, etching of BARC alone is performed, and after the etching system is exchanged, etching of the resist middle layer 4 is performed.

EXAMPLE

Synthesis Examples and Examples are given below together with Comparative Examples for further illustrating the invention although the invention is not limited thereby.

The weight average molecular weight (Mw) and number average molecular weight (Mn) of a polymer are determined versus polystyrene standards by GPC using tetrahydrofuran as solvent, and a dispersity (Mw/Mn) is computed therefrom. THF is tetrahydrofuran, and MIBK is methyl isobutyl ketone.

Synthesis Example 1

Synthesis of Biphenyl Derivative (9)

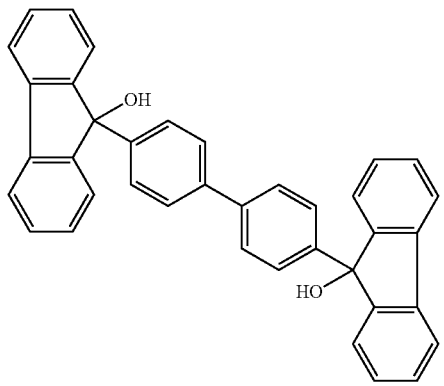

In a nitrogen atmosphere, 26.4 g (1.09 mol) of magnesium was weighed and fed into a 5-L four-neck flask, to which a portion of a solution of 168 g (0.54 mol) of 4,4'-dibromobiphenyl and 23.0 g (0.54 mol) of lithium chloride in 1,000 ml of dry THF was added until the magnesium was immersed therein. An amount of dibromoethane was added whereupon reaction started. The remaining portion of the THF solution was added dropwise over 3 hours while maintaining the exothermic reaction. At the end of dropwise addition, 500 ml of THF was added to the reaction solution, which was ripened for 8 hours under reflux to form a Grignard reagent. The flask was cooled to an internal temperature of 55° C., whereupon a solution of 150 g (0.83 mol) of 9-fluorenone in 400 ml of dry THF was added dropwise over 2 hours. At the end of dropwise addition, the solution was ripened for 5.5 hours under reflux. The flask was cooled in an ice bath, whereupon 1,000 ml of saturated ammonium chloride aqueous solution and 1,000 ml of deionized water were added to quench the reaction. A white precipitate formed in the solution, which became a suspension. To the reaction solution was added 150 ml of MIBK. The resulting suspension was transferred to a separatory funnel, from which the water layer was discharged. After further separatory washing with 500 ml of deionized water, the organic layer was concentrated in vacuum. The concentrate was recrystallized from diisopropyl ether. The resulting white crystal was filtered and dried, obtaining 109 g (yield 51.0%) of biphenyl derivative (9).

Biphenyl Derivative (9):

IR (D-ATR): ν=3539, 3064, 3039, 1605, 1495, 1447, 1164, 1030, 909, 820, 771, 754, 736 cm$^{-1}$ $^1$H-NMR (600 MHz in DMSO-d$_6$): δ=6.34 (2H, —OH, s), 7.24 (4H, t), 7.27 (8H, d), 7.36 (4H, t-t), 7.45 (4H, d), 7.81 (4H, d) ppm $^{13}$C-NMR (150 MHz in DMSO-d$_6$): δ=82.44, 120.10, 124.66, 125.66, 126.28, 128.07, 128.51, 138.41, 139.14, 144.19, 151.23 ppm Synthesis Example 2

Synthesis of Biphenyl Derivative (10)

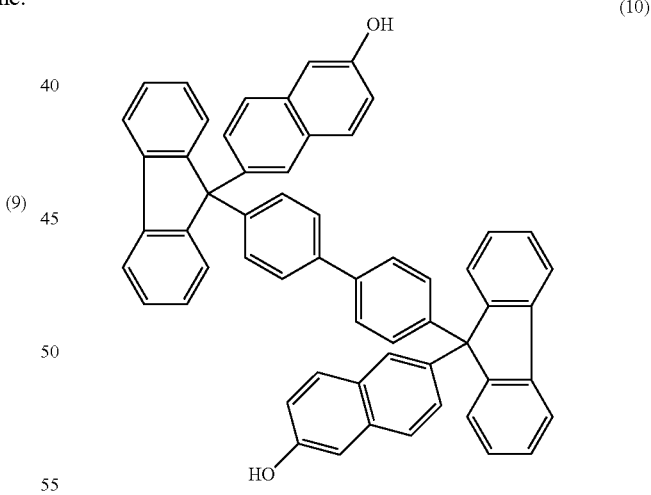

Into a 1-L three-neck flask, 40.3 g (78.4 mmol) of biphenyl derivative (9), 23.73 g (164.6 mmol) of 2-naphthol, and 240 ml of 1,2-dichloroethane were weighed and fed. With stirring in an oil bath at 30° C., 7.3 ml of methanesulfonic acid was slowly added dropwise. At the end of dropwise addition, the temperature of the oil bath was elevated to 50° C., at which reaction run for 6 hours. The reaction solution was allowed to cool down to room temperature, diluted with 500 ml of MIBK, filtered to remove the insoluble matter, and transferred to a separatory funnel. Separatory washing with 300 ml of ultrapure water was repeated 9 times. The organic layer was concentrated in vacuum. The residue was dissolved in 800 ml of THF and poured into 2,500 ml of hexane for crystallization. The crystal was filtered and dried, obtaining 51.6 g (yield 85.8%) of biphenyl derivative (10)

Biphenyl Derivative (10):

IR (KBr): ν=3528, 3389, 3059, 3030, 1633, 1604, 1506, 1493, 1446, 1219, 1181, 750, 740 cm$^{-1}$ $^1$H-NMR (600 MHz in DMSO-d$_6$): δ=6.98 (2H, d-d), 7.05 (2H, s-d), 7.17 (4H, d), 7.24 (2H, d-d), 7.29 (4H, t), 7.38 (4H, t), 7.40 (2H, s), 7.45 (4H, d), 7.50 (6H, d), 7.58 (2H, d), 7.93 (4H, d), 9.72 (2H, —OH, s) ppm $^{13}$C-NMR (150 MHz in DMSO-d$_6$): δ=64.59, 108.35, 118.77, 120.58, 125.19, 126.11, 126.36, 126.62, 126.94, 127.16, 127.71, 127.88, 128.20, 129.35, 133.39, 138.14, 139.26, 139.59, 144.82, 150.56, 155.39 ppm TG-DTA (air; 30→500° C.): −3.92%

TG-DTA (He; 30→500° C.): −17.71%

In air, crosslinking reaction was induced by oxidative coupling reaction accompanied with dehydrogenation reaction at high temperature, indicating that pyrolysis was restrained as compared in He. The derivative exhibited excellent heat resistance as demonstrated by a weight loss of only 3.92% on heating at 500° C. in air.

Synthesis Example 3

Synthesis of Biphenyl Derivative (11)

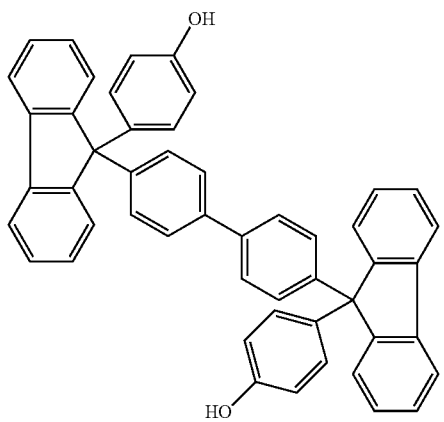

(11)

Into a 200-ml three-neck flask, 10.0 g (19.0 mmol) of biphenyl derivative (9), 3.66 g (39.0 mmol) of phenol, and 60 ml of 1,2-dichloroethane were weighed and fed. With stirring in a water bath, 2.4 ml of methanesulfonic acid was slowly added dropwise. At the end of dropwise addition, the temperature of an oil bath was elevated to 50° C., at which reaction run for 2 hours. The reaction solution was allowed to cool down to room temperature, diluted with 150 ml of MIBK, filtered to remove the insoluble matter, and transferred to a separatory funnel. Separatory washing with 100 ml of ultrapure water was repeated 4 times. The organic layer was concentrated in vacuum. The residue was dissolved in 28.8 g of THF and poured into 900 ml of hexane for crystallization. The crystal was filtered and dried, obtaining 8.3 g (yield 65.5%) of biphenyl derivative (11).

Biphenyl Derivative (11):

IR (KBr): ν=3501, 3371, 3031, 1693, 1604, 1594, 1508, 1446, 1174 cm$^{-1}$ $^1$H-NMR (600 MHz in DMSO-d$_6$): δ=6.63 (4H, d), 6.93 (4H, d), 7.12 (4H, d), 7.28 (4H, dd), 7.36 (4H, dd), 7.41 (4H, d), 7.43 (4H, d), 7.89 (4H, d), 9.33 (2H, —OH, s) ppm $^{13}$C-NMR (150 MHz in DMSO-d$_6$): δ=63.99, 115.02, 120.43, 125.98, 126.49, 127.50, 127.77, 128.06, 128.74, 135.26, 138.05, 139.42, 145.18, 150.99, 156.12 ppm Synthesis Example 4

Synthesis of Biphenyl Derivative (12)

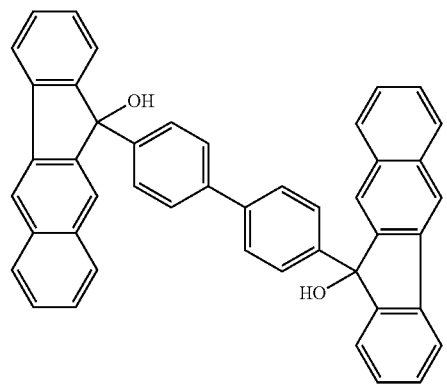

(12)

In a nitrogen atmosphere, 24.3 g (1.00 mol) of magnesium was weighed and fed into a 5-L four-neck flask, to which a portion of a solution of 156 g (0.50 mol) of 4,4'-dibromobiphenyl and 22.5 g (0.53 mol) of lithium chloride in 1,000 ml of dry THF was added until the magnesium was immersed therein. An amount of dibromoethane was added whereupon reaction started. The remaining portion of the THF solution was added dropwise over 5 hours while maintaining the exothermic reaction. At the end of dropwise addition, 500 ml of THF was added to the reaction solution, which was ripened for 4 hours under reflux to form a Grignard reagent. The flask was cooled to an internal temperature of 50° C., a suspension of 177.3 g (0.77 mol) of 9-benzo[b]fluorenone in 1,500 ml of dry THF was added dropwise over 30 minutes. At the end of dropwise addition, the solution was ripened for 5 hours under reflux. The flask was cooled in an ice bath, whereupon 1,000 ml of saturated ammonium chloride aqueous solution was added to quench the reaction. The reaction solution was combined with 500 ml of MIBK and transferred to a separatory funnel, from which the water layer was discharged. After further separatory washing with 500 ml of deionized water and saturated saline, the organic layer was dried over magnesium sulfate. After filtration of the drying agent and distillation of the solvent, the residue was purified by column chromatography, obtaining 53.2 g (yield 21.1%) of biphenyl derivative (12).

Biphenyl Derivative (12):

IR (KBr): ν=3543, 3427, 3050, 1637, 1607, 1504, 1494, 1251, 1168, 1038, 882, 817, 781, 755 cm$^{-1}$ $^1$H-NMR (600 MHz in DMSO-d$_6$): δ=6.49 (2H, —OH, s), 7.29-7.32 (8H, m), 7.41-7.48 (10H, m), 7.75 (2H, s), 7.86 (2H, d), 7.95 (2H, d), 7.97 (2H, d), 8.31 (2H, d) ppm $^{13}$C-NMR (150 MHz in DMSO-d$_6$): δ=82.03, 118.21, 120.72, 123.52, 125.05, 125.75, 125.83, 126.22, 126.31, 128.03, 128.33, 128.84, 128.87, 133.35, 133.64, 137.85, 138.40, 138.59, 144.90, 149.64, 151.07 ppm Synthesis Example 5

Synthesis of Biphenyl Derivative (13)

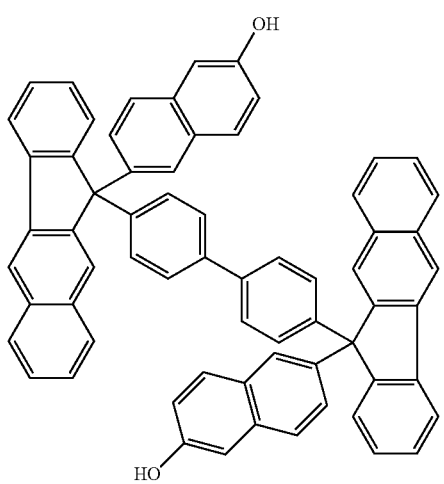

Into a 1-L three-neck flask, 5.0 g (8.13 mmol) of biphenyl derivative (12), 2.58 g (17.9 mmol) of 2-naphthol, and 30 ml of 1,2-dichloroethane were weighed and fed. With stirring at room temperature, 1.5 ml of methanesulfonic acid was slowly added dropwise. At room temperature, reaction run for 4 hours. The reaction solution was diluted with 100 ml of ethyl acetate, filtered to remove the insoluble matter, and transferred to a separatory funnel. Separatory washing with 30 ml of ultrapure water was repeated 7 times. The organic layer was concentrated in vacuum. The residue was poured into methanol for crystallization, obtaining 6.4 g (yield 90.8%) of biphenyl derivative (13).

Biphenyl Derivative (13):

IR (KBr): ν=3545, 3325, 3048, 1634, 1604, 1505, 1492, 1433, 1216, 1176, 875, 750 cm$^{-1}$ $^1$H-NMR (600 MHz in DMSO-d$_6$): δ=6.97 (2H, d-d), 7.06 (2H, s-d), 7.21 (4H, d), 7.32 (4H, t), 7.40-7.50 (16H, m), 7.60 (2H, d), 7.83 (2H, d), 7.96-7.98 (4H, m), 8.06 (2H, d), 8.43 (2H, d), 9.72 (2H, —OH, s) ppm $^{13}$C-NMR (150 MHz in DMSO-d$_6$): δ=64.21, 108.35, 118.62, 118.77, 121.13, 124.89, 125.40, 125.81, 126.14, 126.40, 126.59, 127.01, 127.16, 127.97, 128.23, 128.33, 128.68, 129.43, 132.98, 133.10, 133.35, 138.04, 138.44, 138.93, 139.87, 145.42, 148.98, 150.91, 155.40 ppm TG-DTA (air; 30→500° C.): 4.58%

TG-DTA (He; 30→500° C.): 11.44%

In air, crosslinking reaction was induced by oxidative coupling reaction accompanied with dehydrogenation reaction at high temperature, indicating that pyrolysis was restrained as compared in He. The derivative exhibited excellent heat resistance as demonstrated by a weight loss of only 4.58% on heating at 500° C. in air.

Synthesis Example 6

Synthesis of Biphenyl Derivative (14)

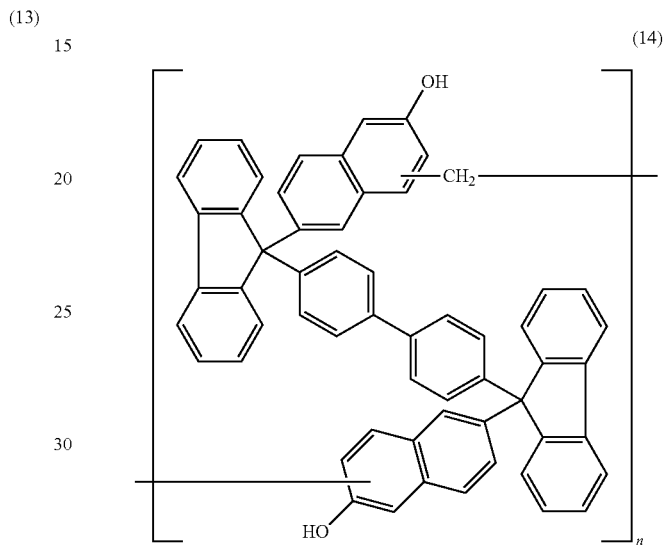

Herein, n is a number providing a Mw reported in Table 2.

Into a 200-ml three-neck flask, 10.0 g (13.0 mmol) of biphenyl derivative (10) and 30 ml of 1-methoxy-2-propanol were weighed and fed. With the flask placed in an oil bath at 75° C., the contents were stirred in N$_2$ atmosphere until dissolved. To the flask, 0.25 g (7.8 mmol) of paraformaldehyde was added, and 2.5 g of a 20 wt % solution of p-toluenesulfonic acid monohydrate in 1-methoxy-2-propanol was added dropwise. At the end of dropwise addition, the temperature of the oil bath was elevated to 85° C., at which reaction run for 4 hours. The reaction solution was allowed to cool down to room temperature, diluted with 100 ml of MIBK, filtered to remove the insoluble matter, and transferred to a separatory funnel. Separatory washing with 30 ml of ultrapure water was repeated 8 times. The organic layer was concentrated in vacuum. The polymer was recovered and dried in vacuum, obtaining 10.0 g (yield 99%) of biphenyl derivative (14).

Biphenyl Derivative (14):

IR (ATR): ν=3459, 3344, 3027, 2954, 1696, 1601, 1493, 1447, 1277, 1210 cm$^{-1}$

Mw=4,921

Mw/Mn=1.75

TG-DTA (air; 30→500° C.): −22.48%

TG-DTA (He; 30→500° C.): −20.20%

The weight loss on heating from 300° C. to 500° C. was 12.65% in He and 10.62% in air. In air, crosslinking reaction was induced by oxidative coupling reaction accompanied with dehydrogenation reaction at high temperature, indicating that pyrolysis was restrained as compared in He.

Synthesis Example 7

Synthesis of Biphenyl Derivative (15)

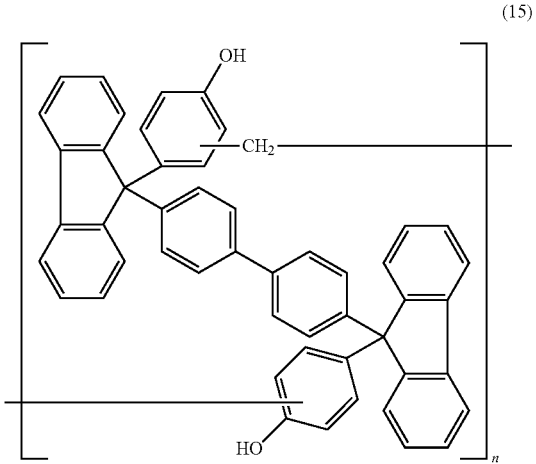

(15)

Herein, n is a number providing a Mw reported in Table 2.

Into a 100-ml three-neck flask, 2.0 g (3.0 mmol) of biphenyl derivative (11) and 10 ml of 1-methoxy-2-propanol were weighed and fed. With the flask placed in an oil bath at 75° C., the contents were stirred in $N_2$ atmosphere until dissolved. To the flask, 0.057 g (1.8 mmol) of paraformaldehyde was added, and 0.5 g of a 20 wt % solution of p-toluenesulfonic acid monohydrate in 1-methoxy-2-propanol was added dropwise. At the end of dropwise addition, the temperature of the oil bath was elevated to 85° C., at which reaction run for 4 hours. The reaction solution was allowed to cool down to room temperature, diluted with 50 ml of MIBK, filtered to remove the insoluble matter, and transferred to a separatory funnel. Separatory washing with 20 ml of ultrapure water was repeated 8 times. The organic layer was concentrated in vacuum. The polymer was recovered and dried in vacuum, obtaining 2.0 g (yield 98%) of biphenyl derivative (15).

Biphenyl Derivative (15):
IR (ATR): ν=3500, 3343, 3028, 2955, 1698, 1607, 1507, 1493, 1263, 1224, 1174 $cm^{-1}$
Mw=15,881
Mw/Mn=7.52
TG-DTA (air; 30→500° C.): −25.11%
TG-DTA (He; 30→500° C.): −36.60%

The weight loss on heating from 300° C. to 500° C. was 24.62% in He and 13.44% in air. In air, crosslinking reaction was induced by oxidative coupling reaction accompanied with dehydrogenation reaction at high temperature, indicating that pyrolysis was restrained as compared in He.

Table 1 tabulates Compounds 1, 2 and 3 which correspond to biphenyl derivatives (10), (11) and (13) obtained in Synthesis Examples 2, 3 and 5, respectively. Table 2 tabulates Polymers 1 and 2 which correspond to biphenyl derivatives (14) and (15) obtained in Synthesis Examples 6 and 7, respectively. Table 3 tabulates Binder Polymers 3, 4, and 5, thermal acid generator TAG1, and crosslinker XL1. Table 4 tabulates Comparative Polymers 6 and 7, and Comparative Additive 1.

Bottom layer materials in solution form were prepared by dissolving a binder polymer, biphenyl derivative, acid generator, and crosslinker in a solvent in accordance with the formulation shown in Tables 5 and 6 and filtering through a fluoroplastic filter with a pore size of 0.1 μm. The solvent contained a surfactant FC-4430 (3M-Sumitomo Co., Ltd.).

It is noted that the synthesis of Binder Polymers 3 and 4 is described in the following synthesis examples.

TABLE 1

| | Synthesis Example |
|---|---|
| Compound 1 | Synthesis Example 2 Biphenyl derivative (10) |

TABLE 1-continued

| | | Synthesis Example |
|---|---|---|
| Compound 2 | [structure] | Synthesis Example 3 Biphenyl derivative (11) |
| Compound 3 | [structure] | Synthesis Example 5 Biphenyl derivative (13) |

TABLE 2

| | | Synthesis Example | Mw | Mw/Mn |
|---|---|---|---|---|
| Polymer 1 | [structure] | Synthesis Example 6 Biphenyl derivative (14) | 4,921 | 1.75 |

TABLE 2-continued

| | | Synthesis Example | Mw | Mw/Mn |
|---|---|---|---|---|
| Polymer 2 | (structure) | Synthesis Example 7 Biphenyl derivative (15) | 15,881 | 7.52 |

TABLE 3

| | | Synthesis Example | Mw | Mw/Mn |
|---|---|---|---|---|
| Binder Polymer 3 | (structure) | Synthesis Example 8 Naphthalene derivative (1) | 2,867 | 1.95 |
| Binder Polymer 4 | (structure) | Synthesis Example 9 Naphthalene derivative (2) | 3,013 | 1.57 |
| Binder Polymer 5 | (structure) | — | 4,300 | 4.30 |

TABLE 3-continued

| | | Synthesis Example | Mw | Mw/Mn |
|---|---|---|---|---|
| TAG1 | (triethylammonium nonaflate: Et₃NH⁺ CF₃CF₂CF₂CF₂SO₃⁻) | — | — | — |
| XL1 | (tetramethoxymethyl glycoluril) | — | — | — |

TABLE 4

| | | Mw | Mw/Mn |
|---|---|---|---|
| Comparative Polymer 6 | (acenaphthylene/4-hydroxystyrene copolymer, 0.8/0.2) | 7,600 | 1.96 |
| Comparative Polymer 7 | (bisphenolfluorene-CH₂ polymer) | 13,000 | 4.33 |
| Comparative Additive 1 | (bis-naphthol fluorene compound) | — | — |

Synthesis Example 8

Synthesis of Naphthalene Derivative (1)

Naphthalene derivative (1)

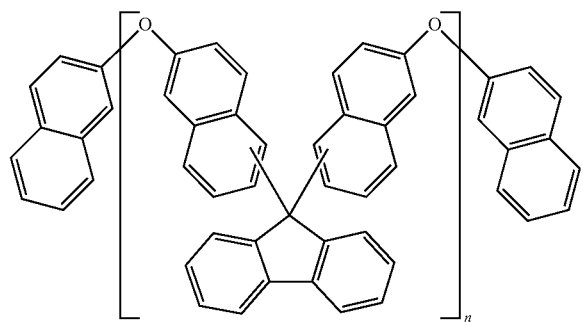

A three-neck flask was charged with 30.0 g (111 mmol) of 2,2'-dinaphthyl ether, 20.0 g (111 mmol) of 9-fluorenone, and 120 ml of 1,2-dichloroethane, which were dissolved by keeping the flask in an oil bath. After dissolution was confirmed, 0.6 ml of 3-mercaptopropionic acid and 6.0 ml of methanesulfonic acid were added dropwise. Under reflux, reaction was effected for 13 hours. At the end of reaction, the reaction solution was diluted with 500 ml of toluene, and transferred to a separatory funnel where it was washed with water and separated. Water washing was repeated until the water layer became neutral. The organic layer was concentrated under reduced pressure. The residue was combined with 250 ml of THF and poured into 2,250 ml of hexane, allowing the polymer to crystallize. The polymer was dried in vacuum, obtaining naphthalene derivative (1).

Naphthalene Derivative (1)
 Mw=2,867
 Mw/Mn=1.95
 IR (KBr): ν=3055, 1910, 1596, 1502, 1463, 1255, 1219, 1193, 1165 cm$^{-1}$
 n=~6.0 (computed from Mw), ~5.45 (computed from $^{13}$C-NMR)

Synthesis Example 9

Synthesis of Naphthalene Derivative (2)

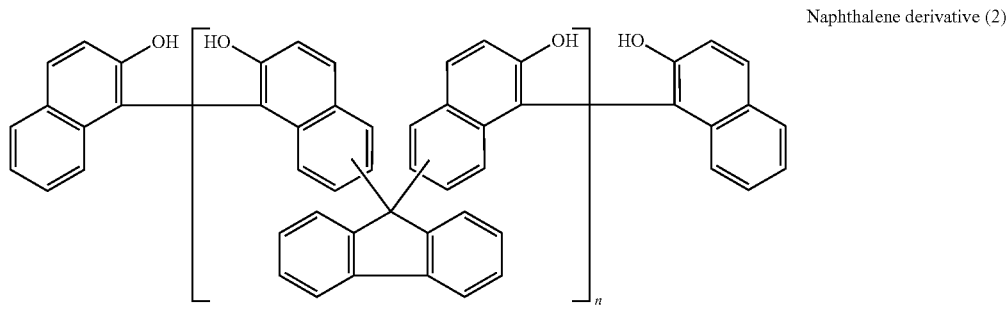

Naphthalene derivative (2)

A three-neck flask was charged with 15.9 g (5.6 mmol) of 1,1'-bi-2,2'-naphthol, 10.0 g (5.6 mmol) of 9-fluorenone, and 125 ml of 1,2-dichloroethane, which were dissolved by keeping the flask in an oil bath. After dissolution was confirmed, 0.3 ml of 3-mercaptopropionic acid and 3.0 ml of methanesulfonic acid were added dropwise. Under reflux, reaction was effected for 10 hours. At the end of reaction, the reaction solution was diluted with 300 ml of ethyl acetate, and transferred to a separatory funnel where it was washed with water and separated. Water washing was repeated until the water layer became neutral. The organic layer was concentrated under reduced pressure. The residue was combined with 100 ml of THF and poured into 1,300 ml of hexane, allowing the polymer to crystallize. The crystallized polymer was filtered and dried in vacuum, obtaining naphthalene derivative (2).

Naphthalene Derivative (2):
 Mw=3,013
 Mw/Mn=1.57
 IR (KBr): ν=3529, 3060, 2969, 1912, 1620, 1596, 1500, 1474, 1447, 1383, 1343, 1276, 1217, 1147 cm$^{-1}$
 n=~6.08 (computed from Mw), ~4.87 (computed from $^{1}$H-NMR)

TABLE 5

| Formulation | | Biphenyl derivative (pbw) | Binder polymer/ Additive (pbw) | Acid generator (pbw) | Crosslinker (pbw) | Solvent (pbw) | Bake temp./time | Refractive index @193 nm | |
|---|---|---|---|---|---|---|---|---|---|
| | | | | | | | | n value | k value |
| UDL | 1 | Compound 1 (15) | — | — | — | PGMEA(70) CyH(30) | 350° C./ 60 sec | 1.30 | 0.44 |
| | 2 | Compound 2 (15) | — | — | — | PGMEA(70) CyH(30) | 350° C./ 60 sec | 1.30 | 0.44 |
| | 3 | Compound 3 (15) | — | — | — | PGMEA(70) CyH(30) | 350° C./ 60 sec | 1.30 | 0.44 |
| | 4 | Polymer 1 (15) | — | — | — | PGMEA(70) CyH(30) | 350° C./ 60 sec | 1.30 | 0.44 |
| | 5 | Polymer 2 (15) | — | — | — | PGMEA(70) CyH(30) | 350° C./ 60 sec | 1.30 | 0.44 |
| | 6 | Compound 1 (7.5) | Polymer 1 (7.5) | — | — | PGMEA(70) CyH(30) | 350° C./ 60 sec | 1.30 | 0.44 |
| | 7 | Compound 2 (7.5) | Polymer 1 (7.5) | — | — | PGMEA(70) CyH(30) | 350° C./ 60 sec | 1.30 | 0.44 |
| | 8 | Compound 3 (7.5) | Polymer 1 (7.5) | — | — | PGMEA(70) CyH(30) | 350° C./ 60 sec | 1.30 | 0.44 |
| | 9 | Compound 1 (7.5) | Polymer 2 (7.5) | — | — | PGMEA(70) CyH(30) | 350° C./ 60 sec | 1.30 | 0.44 |
| | 10 | Compound 2 (7.5) | Polymer 2 (7.5) | — | — | PGMEA(70) CyH(30) | 350° C./ 60 sec | 1.30 | 0.44 |
| | 11 | Compound 3 (7.5) | Polymer 2 (7.5) | — | — | PGMEA(70) CyH(30) | 350° C./ 60 sec | 1.30 | 0.44 |
| | 12 | Compound 1 (7.5) | Binder Polymer 3 (7.5) | — | — | PGMEA(70) CyH(30) | 350° C./ 60 sec | 1.30 | 0.44 |
| | 13 | Compound 1 (7.5) | Binder Polymer 4 (7.5) | — | — | PGMEA(70) CyH(30) | 350° C./ 60 sec | 1.30 | 0.44 |
| | 14 | Compound 1 (7.5) | Binder Polymer 5 (7.5) | — | — | PGMEA(70) CyH(30) | 350° C./ 60 sec | 1.30 | 0.44 |
| | 15 | Compound 2 (7.5) | Binder Polymer 3 (7.5) | — | — | PGMEA(70) CyH(30) | 350° C./ 60 sec | 1.30 | 0.44 |
| | 16 | Compound 3 (7.5) | Binder Polymer 3 (7.5) | — | — | PGMEA(70) | 350° C./ | | |

TABLE 5-continued

| Formulation | Biphenyl derivative (pbw) | Binder polymer/ Additive (pbw) | Acid generator (pbw) | Crosslinker (pbw) | Solvent (pbw) | Bake temp./time | Refractive index @193 nm n value | k value |
|---|---|---|---|---|---|---|---|---|
| | (7.5) | (7.5) | | | CyH(30) | 60 sec | | |
| 17 | Compound 1 (15) | — | TAG1(2) | XL1(10) | PGMEA(70) CyH(30) | 230° C./ 60 sec | 1.30 | 0.44 |
| 18 | Compound 2 (15) | — | TAG1(2) | XL1(10) | PGMEA(70) CyH(30) | 230° C./ 60 sec | 1.30 | 0.44 |
| 19 | Compound 3 (15) | — | TAG1(2) | XL1(10) | PGMEA(70) CyH(30) | 230° C./ 60 sec | 1.30 | 0.44 |
| 20 | Polymer 1 (15) | — | TAG1(2) | XL1(10) | PGMEA(70) CyH(30) | 230° C./ 60 sec | 1.30 | 0.44 |

PGMEA: propylene glycol monomethyl ether acetate
CyH: cyclohexanone

TABLE 6

| | Formulation | Biphenyl derivative (pbw) | Binder polymer/ Additive (pbw) | Acid generator (pbw) | Crosslinker (pbw) | Solvent (pbw) | Bake temp./time | Refractive index @193 nm n value | k value |
|---|---|---|---|---|---|---|---|---|---|
| UDL | 21 | Polymer 2 (15) | — | TAG1(2) | XL1(10) | PGMEA(70) CyH(30) | 230° C./ 60 sec | 1.30 | 0.44 |
| | 22 | Compound 1 (7.5) | Polymer 1 (7.5) | TAG1(2) | XL1(10) | PGMEA(70) CyH(30) | 230° C./ 60 sec | 1.30 | 0.44 |
| | 23 | Compound 2 (7.5) | Polymer 1 (7.5) | TAG1(2) | XL1(10) | PGMEA(70) CyH(30) | 230° C./ 60 sec | 1.30 | 0.44 |
| | 24 | Compound 3 (7.5) | Polymer 1 (7.5) | TAG1(2) | XL1(10) | PGMEA(70) CyH(30) | 230° C./ 60 sec | 1.30 | 0.44 |
| | 25 | Compound 1 (7.5) | Polymer 2 (7.5) | TAG1(2) | XL1(10) | PGMEA(70) CyH(30) | 230° C./ 60 sec | 1.30 | 0.44 |
| | 26 | Compound 2 (7.5) | Polymer 2 (7.5) | TAG1(2) | XL1(10) | PGMEA(70) CyH(30) | 230° C./ 60 sec | 1.30 | 0.44 |
| | 27 | Compound 3 (7.5) | Polymer 2 (7.5) | TAG1(2) | XL1(10) | PGMEA(70) CyH(30) | 230° C./ 60 sec | 1.30 | 0.44 |
| | 28 | Compound 1 (7.5) | Binder Polymer 3 (7.5) | TAG1(2) | XL1(10) | PGMEA(70) CyH(30) | 230° C./ 60 sec | 1.30 | 0.44 |
| | 29 | Compound 1 (7.5) | Binder Polymer 4 (7.5) | TAG1(2) | XL1(10) | PGMEA(70) CyH(30) | 230° C./ 60 sec | 1.30 | 0.44 |
| | 30 | Compound 1 (7.5) | Binder Polymer 5 (7.5) | TAG1(2) | XL1(10) | PGMEA(70) CyH(30) | 230° C./ 60 sec | 1.30 | 0.44 |
| | 31 | Compound 2 (7.5) | Binder Polymer 3 (7.5) | TAG1(2) | XL1(10) | PGMEA(70) CyH(30) | 230° C./ 60 sec | 1.30 | 0.44 |
| | 32 | Compound 3 (7.5) | Binder Polymer 3 (7.5) | TAG1(2) | XL1(10) | PGMEA(70) CyH(30) | 230° C./ 60 sec | 1.30 | 0.44 |
| Comparative UDL | 1 | Comparative Additive 1 (15) | — | — | — | PGMEA(100) | 230° C./ 60 sec | film could not be formed | |
| | 2 | Binder Polymer 5 (15) | — | — | — | PGMEA(100) | 350° C./ 60 sec | 1.31 | 0.44 |
| | 3 | Binder Polymer 5 (7.5) | Comparative Additive 1 (7.5) | — | — | PGMEA(100) | 350° C./ 60 sec | 1.31 | 0.44 |
| | 4 | Binder Polymer 5 (7.5) | Comparative Additive 1 (7.5) | TAG1(2) | XL1(10) | PGMEA(100) | 230° C./ 60 sec | 1.31 | 0.44 |
| | 5 | Comparative Polymer 6 (7.5) | Binder Polymer 5 (7.5) | TAG1(2) | XL1(10) | PGMEA(100) | 230° C./ 60 sec | 1.50 | 0.30 |
| | 6 | Comparative Polymer 6 (7.5) | Comparative Polymer 7 (7.5) | TAG1(2) | XL1(10) | PGMEA(100) | 230° C./ 60 sec | 1.50 | 0.30 |

Measurement of Refractive Index

Each of the resist bottom layer material solutions formulated in Tables 5 and 6 was coated onto a silicon substrate and baked at 350° C. for 60 seconds in UDL-1 to 16 and Comparative UDL-2, 3 or at 230° C. for 60 seconds in UDL-17 to 32 and Comparative UDL-1, 4 to 6 to form a bottom (or undercoat) layer of 200 nm thick. Notably, a film could not be formed in Comparative UDL-1. Using a variable angle spectroscopic ellipsometer (VASE®) of J. A. Woollam Co., the refractive index (n, k) at wavelength 193 nm of the bottom layers (UDL-1 to 32, Comparative UDL-2 to 6) was determined. The results are also shown in Tables 5 and 6.

Examples 1 to 47 & Comparative Examples 1 to 7

Evaluation of Solvent Resistance: Loss of Film Thickness by Solvent Treatment

Each of the resist bottom layer material solutions (UDL-1 to 32 and Comparative UDL-2 to 6) was coated onto a silicon substrate and baked in air at the temperature shown in Tables 7 and 8 for 60 seconds to form a bottom layer film. The film thickness was measured. PGMEA was dispensed on the film and kept thereon for 30 seconds, after which the substrate was spin dried and baked at 100° C. for 60 seconds for evaporating off the PGMEA. At this point, the film thickness was measured again, determining a difference in film thickness before and after PGMEA treatment. The results are shown in Tables 7 and 8.

$CF_4/CHF_3$ Base Gas Etching Test

Each of the resist bottom layer material solutions (UDL-1 to 32 and Comparative UDL-2 to 6) was coated onto a silicon substrate and baked in air at the temperature shown in Tables 7 and 8 for 60 seconds to form a bottom layer film of 350 nm thick. These bottom layer films were examined by a test of etching with $CF_4/CHF_3$ base gas using a dry etching instrument TE-8500 by Tokyo Electron, Ltd. A difference in thickness of the film before and after the etching test was determined. The results are also shown in Tables 7 and 8.

| $CF_4/CHF_3$ base gas etching test | |
|---|---|
| Chamber pressure | 40.0 Pa |
| RF power | 1000 W |
| $CHF_3$ gas flow rate | 10 ml/min |
| $CF_4$ gas flow rate | 100 ml/min |
| He gas flow rate | 200 ml/min |
| Time | 20 sec |

In Tables 7 and 8, a film thickness loss by $CF_4/CHF_3$ base gas etching is reported in a relative value (percent), provided that the film thickness loss in Comparative Example 2 is 100. A lower percent film thickness loss indicates greater etch resistance.

$O_2$ Base Gas Etching Test

Each of the resist bottom layer material solutions (UDL-1 to 32 and Comparative UDL-2 to 6) was coated onto a silicon substrate and baked in air at the temperature shown in Tables 7 and 8 for 60 seconds to form a bottom layer film of 350 nm thick. These bottom layer films were examined by a test of etching with $O_2$ base gas using a dry etching instrument TE-8500 by Tokyo Electron, Ltd. A difference in thickness of the film before and after the etching test was determined. The results are also shown in Tables 7 and 8.

| $O_2$ base gas etching test | |
|---|---|
| Chamber pressure | 40.0 Pa |
| RF power | 100 W |
| $O_2$ gas flow rate | 30 ml/min |
| $N_2$ gas flow rate | 70 ml/min |
| Time | 60 sec |

In Tables 7 and 8, a film thickness loss by $O_2$ base gas etching is reported in a relative value (percent), provided that the film thickness loss in Comparative Example 2 is 100. A lower percent film thickness loss indicates greater etch resistance.

TABLE 7

| | | Formulation | Bake temp./time | Loss of film thickness by solvent treatment, Å | Loss of film thickness by $CF_4/CHF_3$ gas etching | | Loss of film thickness by $O_2$ gas etching | |
|---|---|---|---|---|---|---|---|---|
| | | | | | Å | percent loss based on film loss in CE2 = 100 | Å | percent loss based on film loss in CE2 = 100 |
| Example | 1 | UDL-1 | 350° C./60 sec | 1 | 546 | 92% | 2092 | 96% |
| | 2 | UDL-2 | 350° C./60 sec | 7 | 550 | 97% | 2116 | 97% |
| | 3 | UDL-3 | 350° C./60 sec | 1 | 542 | 91% | 2087 | 96% |
| | 4 | UDL-4 | 350° C./60 sec | 10 | 545 | 92% | 2106 | 97% |
| | 5 | UDL-5 | 350° C./60 sec | 9 | 550 | 92% | 2110 | 97% |
| | 6 | UDL-6 | 350° C./60 sec | 1 | 576 | 97% | 2147 | 99% |
| | 7 | UDL-7 | 350° C./60 sec | 2 | 577 | 97% | 2149 | 99% |
| | 8 | UDL-8 | 350° C./60 sec | 1 | 574 | 97% | 2139 | 98% |
| | 9 | UDL-9 | 350° C./60 sec | 3 | 575 | 97% | 2149 | 99% |
| | 10 | UDL-10 | 350° C./60 sec | 4 | 578 | 97% | 2154 | 99% |
| | 11 | UDL-11 | 350° C./60 sec | 4 | 575 | 97% | 2141 | 98% |
| | 12 | UDL-12 | 350° C./60 sec | 9 | 578 | 97% | 2108 | 97% |
| | 13 | UDL-13 | 350° C./60 sec | 8 | 575 | 97% | 2115 | 97% |
| | 14 | UDL-14 | 350° C./60 sec | 1 | 553 | 93% | 2145 | 98% |
| | 15 | UDL-15 | 350° C./60 sec | 11 | 556 | 94% | 2110 | 97% |
| | 16 | UDL-16 | 350° C./60 sec | 9 | 578 | 97% | 2073 | 95% |
| | 17 | UDL-1 | 400° C./60 sec | 8 | 557 | 94% | 2156 | 99% |
| | 18 | UDL-2 | 400° C./60 sec | 7 | 563 | 96% | 2163 | 99% |
| | 19 | UDL-3 | 400° C./60 sec | 4 | 550 | 92% | 2139 | 98% |
| | 20 | UDL-4 | 400° C./60 sec | 3 | 568 | 96% | 2141 | 98% |
| | 21 | UDL-5 | 400° C./60 sec | 2 | 564 | 95% | 2143 | 98% |
| | 22 | UDL-6 | 400° C./60 sec | 4 | 569 | 96% | 2136 | 98% |
| | 23 | UDL-8 | 400° C./60 sec | 7 | 572 | 96% | 2123 | 97% |
| | 24 | UDL-9 | 400° C./60 sec | 10 | 578 | 97% | 2119 | 97% |

TABLE 7-continued

|  | Formulation | Bake temp./time | Loss of film thickness by solvent treatment, Å | Loss of film thickness by $CF_4/CHF_3$ gas etching | | Loss of film thickness by $O_2$ gas etching | |
|---|---|---|---|---|---|---|---|
|  |  |  |  | Å | percent loss based on film loss in CE2 = 100 | Å | percent loss based on film loss in CE2 = 100 |
| 25 | UDL-10 | 400° C./60 sec | 8 | 582 | 98% | 2131 | 98% |
| 26 | UDL-11 | 400° C./60 sec | 8 | 572 | 96% | 2115 | 97% |
| 27 | UDL-12 | 400° C./60 sec | 0 | 580 | 98% | 2115 | 97% |
| 28 | UDL-13 | 400° C./60 sec | 5 | 576 | 97% | 2121 | 97% |

TABLE 8

|  |  | Formulation | Bake temp./time | Loss of film thickness by solvent treatment, Å | Loss of film thickness by $CF_4/CHF_3$ gas etching | | Loss of film thickness by $O_2$ gas etching | |
|---|---|---|---|---|---|---|---|---|
|  |  |  |  |  | Å | percent loss based on film loss in CE2 = 100 | Å | percent loss based on film loss in CE2 = 100 |
| Example | 29 | UDL-14 | 400° C./60 sec | 1 | 540 | 91% | 2158 | 99% |
|  | 30 | UDL-15 | 400° C./60 sec | 3 | 565 | 95% | 2117 | 97% |
|  | 31 | UDL-16 | 400° C./60 sec | 4 | 588 | 99% | 2095 | 96% |
|  | 32 | UDL-17 | 230° C./60 sec | 3 | 568 | 95% | 2107 | 97% |
|  | 33 | UDL-18 | 230° C./60 sec | 5 | 590 | 99% | 2142 | 98% |
|  | 34 | UDL-19 | 230° C./60 sec | 2 | 566 | 95% | 2093 | 96% |
|  | 35 | UDL-20 | 230° C./60 sec | 1 | 574 | 97% | 2119 | 97% |
|  | 36 | UDL-21 | 230° C./60 sec | 2 | 577 | 97% | 2139 | 98% |
|  | 37 | UDL-22 | 230° C./60 sec | 3 | 571 | 96% | 2110 | 97% |
|  | 38 | UDL-23 | 230° C./60 sec | 3 | 574 | 96% | 2117 | 97% |
|  | 39 | UDL-24 | 230° C./60 sec | 4 | 570 | 96% | 2104 | 97% |
|  | 40 | UDL-25 | 230° C./60 sec | 3 | 575 | 97% | 2130 | 98% |
|  | 41 | UDL-26 | 230° C./60 sec | 2 | 578 | 97% | 2132 | 98% |
|  | 42 | UDL-27 | 230° C./60 sec | 2 | 574 | 96% | 2119 | 97% |
|  | 43 | UDL-28 | 230° C./60 sec | 1 | 549 | 92% | 2073 | 95% |
|  | 44 | UDL-29 | 230° C./60 sec | 6 | 561 | 94% | 2134 | 98% |
|  | 45 | UDL-30 | 230° C./60 sec | 2 | 587 | 99% | 2156 | 99% |
|  | 46 | UDL-31 | 230° C./60 sec | 3 | 567 | 95% | 2112 | 97% |
|  | 47 | UDL-32 | 230° C./60 sec | 1 | 542 | 91% | 2088 | 96% |
| Comparative Example | 1 | Comparative UDL-2 | 350° C./60 sec | 0 | 601 | 101% | 2224 | 102% |
|  | 2 | Comparative UDL-3 | 350° C./60 sec | 0 | 595 | 100% | 2180 | 100% |
|  | 3 | Comparative UDL-2 | 400° C./60 sec | 1 | 660 | 111% | 2354 | 108% |
|  | 4 | Comparative UDL-3 | 400° C./60 sec | 1 | 625 | 105% | 2224 | 102% |
|  | 5 | Comparative UDL-4 | 230° C./60 sec | 5 | 589 | 99% | 2115 | 97% |
|  | 6 | Comparative UDL-5 | 230° C./60 sec | 2 | 571 | 96% | 2158 | 99% |
|  | 7 | Comparative UDL-6 | 230° C./60 sec | 1 | 559 | 94% | 2202 | 101% |

Preparation of Silicon-Containing Middle Layer-Coating Solution

A silicon-containing middle layer-coating solution was prepared by dissolving 2.0 parts by weight of a silicon-containing polymer, shown below, in 100 parts by weight of a solvent PGMEA containing 0.1 wt % of surfactant FC-4430 (3M-Sumitomo Co., Ltd.) and filtering through a fluoroplastic filter having a pore size of 0.1 The solution was coated onto the bottom layer. A middle layer film resulting from the silicon-containing middle layer-coating solution is designated SiL-1.

Silicon-Containing Polymer:

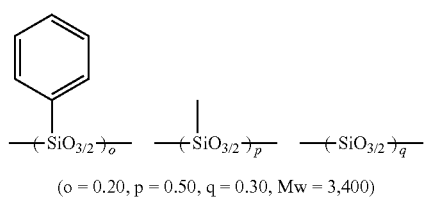

(o = 0.20, p = 0.50, q = 0.30, Mw = 3,400)

Preparation of Resist Top Layer Material and Protective Film for Immersion Lithography A resist top layer material was prepared by dissolving a resin, acid generator and basic compound in a solvent containing 0.1 wt % of surfactant FC-4430 (3M-Sumitomo Co., Ltd.) in accordance with the formulation shown in Table 9 and filtering through a fluoroplastic filter having a pore size of 0.1 µm. Tables 11 and 12, this resist top layer material is designated SL resist for ArF.

TABLE 9

|  | Resin (pbw) | Acid generator (pbw) | Basic compound (pbw) | Solvent (pbw) |
| --- | --- | --- | --- | --- |
| SL resist for ArF | ArF single-layer resist polymer (100) | PAG1 (6.6) | TMMEA (0.8) | PGMEA (2,500) |

The ArF single-layer resist polymer, PAG1, and TMMEA in Table 9 are identified below.

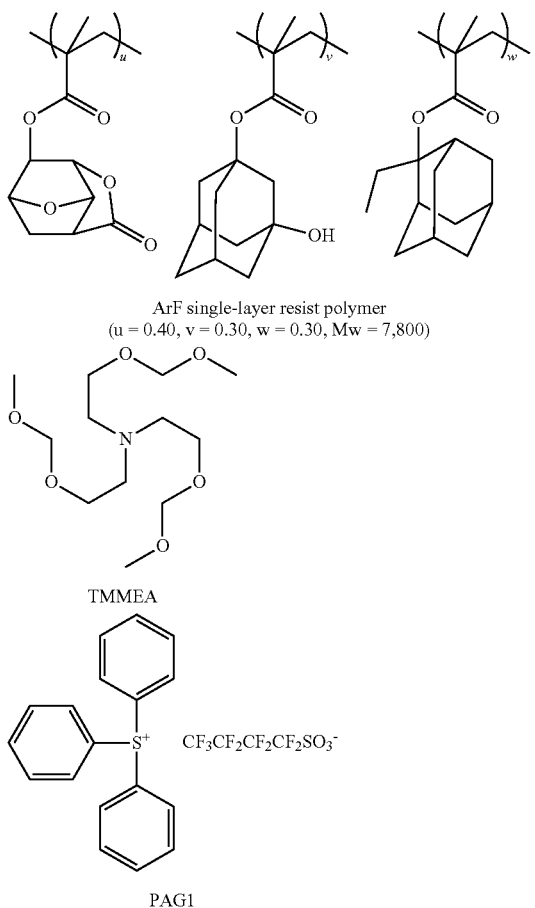

A protective or topcoat film material (TC-1) for immersion lithography was prepared by dissolving a resin in a solvent in accordance with the formulation shown in Table 10 and filtering through a fluoroplastic filter having a pore size of 0.1 µm.

TABLE 10

| Resin (pbw) | Organic solvent (pbw) |
| --- | --- |
| TC-1 protective film polymer (100) | diisoamyl ether (2,700) 2-methyl-1-butanol (270) |

The protective film polymer in Table 10 is identified below.

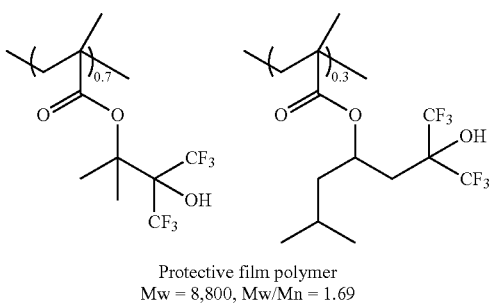

Protective film polymer
Mw = 8,800, Mw/Mn = 1.69

Pattern Etching Test

Examples 48 to 79 & Comparative Examples 8 to 13

Formation of Bottom Layer

The bottom layer material (UDL-1 to 32, Comparative UDL-2 to 6) was coated onto a silicon wafer (diameter 300 mm) having a $SiO_2$ film of 200 nm thick deposited thereon, and baked under the conditions shown in Tables 11 and 12 to form a resist bottom layer of 200 nm thick. The bake of the resist bottom layer was done in an air atmosphere.

Formation of Silicon-Containing Resist Middle Layer SiL-1

The silicon-containing resist middle layer material SiL-1 was coated onto the resist bottom layer and baked at 200° C. for 60 seconds to form a resist middle layer of 35 nm thick.

Formation of Resist Top Layer (SL Resist for ArF) and Protective Film

The resist top layer material (SL resist for ArF in solution form) shown in Tables 11 and 12 was coated on the bottom layer and baked at 105° C. for 60 seconds to form a resist top layer of 100 nm thick. The protective film material (TC-1) for immersion lithography was coated on the resist top layer and baked at 90° C. for 60 seconds to form a protective film of 50 nm thick.

Patterning by Immersion Lithography

The resist top layer was exposed using an ArF immersion lithography exposure tool NSR-S610C (Nikon Corporation, NA 1.30, σ 0.98/0.65, 35° dipole polarized illumination, 6% halftone phase shift mask), baked (PEB) at 100° C. for 60 seconds, and developed for 30 seconds with a 2.38 wt % aqueous solution of tetramethylammonium hydroxide (TMAH), thereby forming a positive 43 nm 1:1 line-and-space pattern.

Etching Test after Patterning

The structure was dry etched using an etching instrument Telius by Tokyo Electron, Ltd. First, the silicon-containing resist middle layer (SOG) was processed through the resist pattern as mask. Then the resist bottom layer was processed through the resulting silicon-containing resist middle layer pattern as mask. Finally, the $SiO_2$ film was processed through the resulting resist bottom layer pattern as mask. The etching conditions are shown below.

Transfer of Resist Pattern to Silicon-Containing Resist Middle Layer

| | |
|---|---|
| Chamber pressure | 10.0 Pa |
| RF power | 1,500 W |
| $CF_4$ gas flow rate | 75 ml/min |
| $O_2$ gas flow rate | 15 ml/min |
| Time | 15 sec |

Transfer of Silicon-Containing Middle Layer Pattern to Bottom Layer

| | |
|---|---|
| Chamber pressure | 2.0 Pa |
| RF power | 500 W |
| Ar gas flow rate | 75 ml/min |
| $O_2$ gas flow rate | 45 ml/min |
| Time | 120 sec |

Transfer of Bottom Layer Pattern to $SiO_2$ Film

| | |
|---|---|
| Chamber pressure | 2.0 Pa |
| RF power | 2,200 W |
| $C_5F_{12}$ gas flow rate | 20 ml/min |
| $C_2F_6$ gas flow rate | 10 ml/min |
| Ar gas flow rate | 300 ml/min |
| $O_2$ gas flow rate | 60 ml/min |
| Time | 90 sec |

The cross-sectional profile of the patterns was observed under electron microscope S-4700 (Hitachi, Ltd.). The results are shown in Tables 11 and 12.

TABLE 11

| | | Bottom layer formulation | Bottom layer bake temp./time | Resist/Middle layer | Pattern profile after development | Pattern profile after etching transfer to middle layer | Pattern profile after etching transfer to bottom layer | Pattern profile after etching transfer to substrate | Pattern twist after etching transfer to substrate |
|---|---|---|---|---|---|---|---|---|---|
| Example | 48 | UDL-1 | 350° C./60 sec | SL resist for ArF/SiL-1 | perpendicular | perpendicular | perpendicular | perpendicular | nil |
| | 49 | UDL-2 | 350° C./60 sec | SL resist for ArF/SiL-1 | perpendicular | perpendicular | perpendicular | perpendicular | nil |
| | 50 | UDL-3 | 350° C./60 sec | SL resist for ArF/SiL-1 | perpendicular | perpendicular | perpendicular | perpendicular | nil |
| | 51 | UDL-4 | 350° C./60 sec | SL resist for ArF/SiL-1 | perpendicular | perpendicular | perpendicular | perpendicular | nil |
| | 52 | UDL-5 | 350° C./60 sec | SL resist for ArF/SiL-1 | perpendicular | perpendicular | perpendicular | perpendicular | nil |
| | 53 | UDL-6 | 350° C./60 sec | SL resist for ArF/SiL-1 | perpendicular | perpendicular | perpendicular | perpendicular | nil |
| | 54 | UDL-7 | 350° C./60 sec | SL resist for ArF/SiL-1 | perpendicular | perpendicular | perpendicular | perpendicular | nil |
| | 55 | UDL-8 | 350° C./60 sec | SL resist for ArF/SiL-1 | perpendicular | perpendicular | perpendicular | perpendicular | nil |
| | 56 | UDL-9 | 350° C./60 sec | SL resist for ArF/SiL-1 | perpendicular | perpendicular | perpendicular | perpendicular | nil |
| | 57 | UDL-10 | 350° C./60 sec | SL resist for ArF/SiL-1 | perpendicular | perpendicular | perpendicular | perpendicular | nil |
| | 58 | UDL-11 | 350° C./60 sec | SL resist for ArF/SiL-1 | perpendicular | perpendicular | perpendicular | perpendicular | nil |
| | 59 | UDL-12 | 350° C./60 sec | SL resist for ArF/SiL-1 | perpendicular | perpendicular | perpendicular | perpendicular | nil |
| | 60 | UDL-13 | 350° C./60 sec | SL resist for ArF/SiL-1 | perpendicular | perpendicular | perpendicular | perpendicular | nil |
| | 61 | UDL-14 | 350° C./60 sec | SL resist for ArF/SiL-1 | perpendicular | perpendicular | perpendicular | perpendicular | nil |
| | 62 | UDL-15 | 350° C./60 sec | SL resist for ArF/SiL-1 | perpendicular | perpendicular | perpendicular | perpendicular | nil |
| | 63 | UDL-16 | 350° C./60 sec | SL resist for ArF/SiL-1 | perpendicular | perpendicular | perpendicular | perpendicular | nil |
| | 64 | UDL-17 | 230° C./60 sec | SL resist for ArF/SiL-1 | perpendicular | perpendicular | perpendicular | perpendicular | nil |
| | 65 | UDL-18 | 230° C./60 sec | SL resist for ArF/SiL-1 | perpendicular | perpendicular | perpendicular | perpendicular | nil |
| | 66 | UDL-19 | 230° C./60 sec | SL resist for ArF/SiL-1 | perpendicular | perpendicular | perpendicular | perpendicular | nil |

TABLE 12

| | | Bottom layer formulation | Bottom layer bake temp./time | Resist/Middle layer | Pattern profile after development | Pattern profile after etching transfer to middle layer | Pattern profile after etching transfer to bottom layer | Pattern profile after etching transfer to substrate | Pattern twist after etching transfer to substrate |
|---|---|---|---|---|---|---|---|---|---|
| Example | 67 | UDL-20 | 230° C./60 sec | SL resist for ArF/SiL-1 | perpendicular | perpendicular | perpendicular | perpendicular | nil |
| | 68 | UDL-21 | 230° C./60 sec | SL resist for ArF/SiL-1 | perpendicular | perpendicular | perpendicular | perpendicular | nil |

TABLE 12-continued

|  |  | Bottom layer formulation | Bottom layer bake temp./time | Resist/Middle layer | Pattern profile after development | Pattern profile after etching transfer to middle layer | Pattern profile after etching transfer to bottom layer | Pattern profile after etching transfer to substrate | Pattern twist after etching transfer to substrate |
|---|---|---|---|---|---|---|---|---|---|
|  | 69 | UDL-22 | 230° C./60 sec | SL resist for ArF/SiL-1 | perpendicular | perpendicular | perpendicular | perpendicular | nil |
|  | 70 | UDL-23 | 230° C./60 sec | SL resist for ArF/SiL-1 | perpendicular | perpendicular | perpendicular | perpendicular | nil |
|  | 71 | UDL-24 | 230° C./60 sec | SL resist for ArF/SiL-1 | perpendicular | perpendicular | perpendicular | perpendicular | nil |
|  | 72 | UDL-25 | 230° C./60 sec | SL resist for ArF/SiL-1 | perpendicular | perpendicular | perpendicular | perpendicular | nil |
|  | 73 | UDL-26 | 230° C./60 sec | SL resist for ArF/SiL-1 | perpendicular | perpendicular | perpendicular | perpendicular | nil |
|  | 74 | UDL-27 | 230° C./60 sec | SL resist for ArF/SiL-1 | perpendicular | perpendicular | perpendicular | perpendicular | nil |
|  | 75 | UDL-28 | 230° C./60 sec | SL resist for ArF/SiL-1 | perpendicular | perpendicular | perpendicular | perpendicular | nil |
|  | 76 | UDL-29 | 230° C./60 sec | SL resist for ArF/SiL-1 | perpendicular | perpendicular | perpendicular | perpendicular | nil |
|  | 77 | UDL-30 | 230° C./60 sec | SL resist for ArF/SiL-1 | perpendicular | perpendicular | perpendicular | perpendicular | nil |
|  | 78 | UDL-31 | 230° C./60 sec | SL resist for ArF/SiL-1 | perpendicular | perpendicular | perpendicular | perpendicular | nil |
|  | 79 | UDL-32 | 230° C./60 sec | SL resist for ArF/SiL-1 | perpendicular | perpendicular | perpendicular | perpendicular | nil |
| Comparative Example | 8 | Comparative UDL-2 | 350° C./60 sec | SL resist for ArF/SiL-1 | perpendicular | perpendicular | perpendicular | perpendicular | heavy twists observed |
|  | 9 | Comparative UDL-3 | 350° C./60 sec | SL resist for ArF/SiL-1 | perpendicular | perpendicular | perpendicular | perpendicular | heavy twists observed |
|  | 10 | Comparative UDL-4 | 350° C./60 sec | SL resist for ArF/SiL-1 | perpendicular | perpendicular | perpendicular | perpendicular | heavy twists observed |
|  | 11 | Comparative UDL-4 | 230° C./60 sec | SL resist for ArF/SiL-1 | perpendicular | perpendicular | perpendicular | perpendicular | heavy twists observed |
|  | 12 | Comparative UDL-5 | 230° C./60 sec | SL resist for ArF/SiL-1 | perpendicular | perpendicular | perpendicular | perpendicular | heavy twists observed |
|  | 13 | Comparative UDL-6 | 230° C./60 sec | SL resist for ArF/SiL-1 | perpendicular | perpendicular | perpendicular | tapered | heavy twists observed |

Step Coverage

Examples 80 to 88 & Comparative Examples 14, 15

On a $SiO_2$ deposited stepped substrate in the form of a silicon substrate having a densely packed hole pattern with a thickness of 500 nm and a diameter of 160 nm formed thereon, a bottom layer material (UDL-1, 2, 3, 6, 7, 8, 12, 14, 16, Comparative UDL-2, 5) was coated and baked at 350° C. for 60 seconds so as to form a bottom layer of 200 nm thick as measured from the flat substrate. The coated substrate was sectioned and observed under SEM whether or not the holes were filled with the film material down to the bottom. The results are shown in Table 13.

TABLE 13

|  | Bottom layer formulation | Bottom layer bake temp./time | Step coverage |
|---|---|---|---|
| Example 80 | UDL-1 | 350° C./60 sec | holes fully filled to bottom |
| Example 81 | UDL-2 | 350° C./60 sec | holes fully filled to bottom |
| Example 82 | UDL-3 | 350° C./60 sec | holes fully filled to bottom |
| Example 83 | UDL-6 | 350° C./60 sec | holes fully filled to bottom |
| Example 84 | UDL-7 | 350° C./60 sec | holes fully filled to bottom |
| Example 85 | UDL-8 | 350° C./60 sec | holes fully filled to bottom |
| Example 86 | UDL-12 | 350° C./60 sec | holes fully filled to bottom |
| Example 87 | UDL-14 | 350° C./60 sec | holes fully filled to bottom |
| Example 88 | UDL-16 | 350° C./60 sec | holes fully filled to bottom |
| Comparative Example 14 | Comparative UDL-2 | 350° C./60 sec | some bury failures |
| Comparative Example 15 | Comparative UDL-5 | 350° C./60 sec | some bury failures |

Outgas Test

Examples 89 to 97 & Comparative Examples 16, 17

A bottom layer material (UDL-1, 2, 3, 6, 7, 8, 12, 14, 16, Comparative UDL-2, 3) was coated on a silicon substrate and baked at 350° C. for 60 seconds to form a bottom layer of 200 nm thick. When particulate emissions were observed in a hot plate oven during the 350° C. bake, the number of particles with a size of 0.3 μm and 0.5 μm was counted using a particle counter KR-11A (Rion Co., Ltd.). The results are shown in Table 14.

TABLE 14

| | Bottom layer formulation | Bottom layer bake temp./time | 0.30 μm particles | 0.50 μm particles |
|---|---|---|---|---|
| Example 89 | UDL-1 | 350° C./60 sec | 9 | 3 |
| Example 90 | UDL-2 | 350° C./60 sec | 56 | 21 |
| Example 91 | UDL-3 | 350° C./60 sec | 8 | 4 |
| Example 92 | UDL-6 | 350° C./60 sec | 4 | 0 |
| Example 93 | UDL-7 | 350° C./60 sec | 12 | 3 |
| Example 94 | UDL-8 | 350° C./60 sec | 10 | 0 |
| Example 95 | UDL-12 | 350° C./60 sec | 5 | 1 |
| Example 96 | UDL-14 | 350° C./60 sec | 8 | 2 |
| Example 97 | UDL-16 | 350° C./60 sec | 7 | 1 |
| Comparative Example 16 | Comparative UDL-2 | 350° C./60 sec | 501 | 120 |
| Comparative Example 17 | Comparative UDL-3 | 350° C./60 sec | 1,010 | 621 |

It is seen from Tables 5 and 6 that the resist bottom layer film formed by the inventive method has such a refractive index that the film may be practically used as the resist bottom layer film in the trilayer process for immersion lithography.

It is seen from Table 6 that Comparative Additive 1 in Comparative UDL-1 could not form a film alone. Comparative UDL-3 indicates that Comparative Additive 1 could not form a film unless Comparative Additive 1 was combined with a binder polymer. In contrast, UDL-1 to 3 wherein biphenyl derivatives, Compounds 1 to 3 were formulated alone could form a film, offering a great advantage.

It is seen from Tables 7 and 8 that baking at a temperature in excess of 350° C. results in a resist bottom layer which is insoluble in the solvent (Examples 1 to 31).

It is seen from Tables 7 and 8 that when thermal acid generator TAG1 and crosslinker XL1 shown in Table 3 are used, a resist bottom layer which is insoluble in the solvent can be formed even by low-temperature baking (Examples 32 to 47). As is also evident from Tables 7 and 8, the rates of $CF_4/CHF_3$ gas etching and $O_2$ gas etching of the resist bottom layer formed by the inventive method are lower than Comparative Examples 1 to 7 (using Binder Polymer 5 and Comparative Polymers 6, 7), indicating very high etch resistance.

It is seen from Tables 11 and 12 that when the resist bottom layer formed by the inventive method was used (Examples 48 to 79), the resist profile after development and the profile of the bottom layer after oxygen etching and after substrate etching were improved, and the patterns were observed to be free of twists.

As seen from Table 13, a burying failure is found in Comparative Examples 14 and 15. In contrast, the present biphenyl derivatives, Compounds 1 to 3 exhibit improved step coverage (Examples 80 to 82) because a film can be formed of the biphenyl derivatives alone without a need for a binder polymer. Step coverage is further improved by adding the present biphenyl derivatives, Compounds 1 to 3 to the resist bottom layer material (Examples 83 to 88).

Comparative Examples 16, 17 in Table 14 show that when a monomer is added for the purpose of improving step coverage, more particles are emitted during bake to contaminate the hot plate oven. Examples 89 to 97 demonstrate that the resist bottom layer formed from the resist bottom layer material comprising the biphenyl derivative as defined herein has both the advantages of step coverage and particle prevention because the biphenyl derivative has heat resistance sufficient to avoid particulate emission.

While the invention has been illustrated and described in typical embodiments, it is not intended to be limited to the details shown. Various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

All the patent documents cited herein are incorporated herein by reference.

Japanese Patent Application No. 2011-069703 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A biphenyl derivative having the general formula (1):

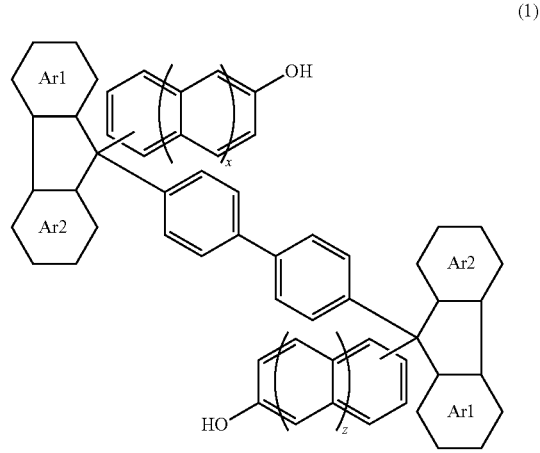

wherein cyclic structures Ar1 and Ar2 denote a benzene or naphthalene ring, x and z are each independently 0 or 1.

2. A biphenyl derivative comprising a partial structure having the general formula (2):

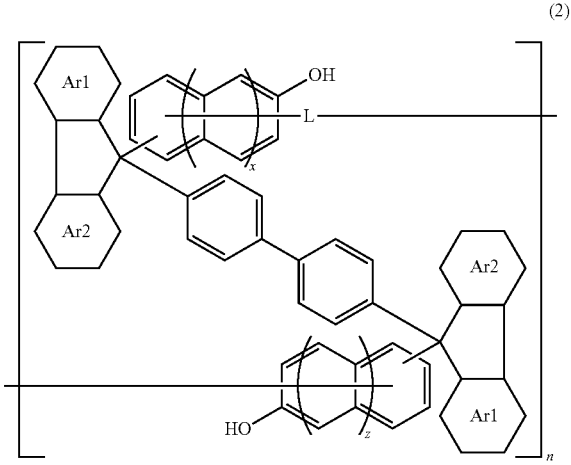

wherein cyclic structures Ar1 and Ar2 denote a benzene or naphthalene ring, x and z are each independently 0 or 1, L is a single bond or a $C_1$-$C_{20}$ alkylene group, and n is such a natural number as to provide a molecular weight of up to 200,000.

3. A resist bottom layer material comprising (i) a biphenyl derivative having formula (1) in claim 1, (ii) a biphenyl derivative comprising a partial structure having formula (2) in claim 2, or (iii) a polymer comprising recurring units of the biphenyl derivative (ii).

4. The resist bottom layer material of claim 3, further comprising an organic solvent.

5. The resist bottom layer material of claim 3, further comprising a crosslinker and an acid generator.

* * * * *